United States Patent [19]
Jones et al.

[11] 3,977,394
[45] Aug. 31, 1976

[54] COMPUTERIZED PULMONARY ANALYZER

[75] Inventors: William C. Jones, Elmhurst, Ill.; Clifford Harwood, Kalamazoo, Mich.

[73] Assignee: Jones Medical Instrument Company, Oak Brook, Ill.

[22] Filed: Feb. 7, 1975

[21] Appl. No.: 548,093

[52] U.S. Cl.............................. 128/2.07; 128/2.08; 73/23; 73/195; 73/421.5 R
[51] Int. Cl.².......................................... A61B 5/08
[58] Field of Search.......................... 128/2.08, 2.07; 73/23 R, 195, 421.5 R

[56] References Cited
UNITED STATES PATENTS

| | | | |
|---|---|---|---|
| 3,726,270 | 4/1973 | Griffis et al. | 128/2.08 |
| 3,739,159 | 6/1973 | Nalley | 73/195 |
| 3,771,512 | 11/1973 | Jones et al. | 128/2.08 |
| 3,785,370 | 1/1974 | Richards | 128/2.08 |

OTHER PUBLICATIONS

Hilberman et al., "On–Line Assessment . . . ill," J. A. Advancement of Med. Inst., vol. 6, Jan.–Feb. 1972, pp. 65–69.
Vallbona et al., "Computer Analysis . . . Status," Computers & Biotled, Research, 4, No. 6, pp. 623–633, (1971).
"Pulmonary Function Study Equipment," Am Journal of Physical Med., vol. 19, No. 3, pp. 208–209, 1970.
Watson et al., "Automated System . . . Breathing," Med. Inst., vol. 9, No. 1, Jan.–Feb. 1975, pp. 3–10.

Primary Examiner—Robert W. Michell
Assistant Examiner—Lee S. Cohen
Attorney, Agent, or Firm—Dawson, Tilton, Fallon & Lungmus

[57] ABSTRACT

A programmable digital computer receives an electrical signal from a spirometer into which a person under test breathes. The signal is representative of the volume of air expired by the person. The computer controls a matrix printer. Data may be entered into the computer via a keyboard. The computer instructs the operator as to when identification data may be entered via the keyboard. The operator indicates which test is to be conducted by actuating the keyboard; and the computer receives the data and indicates whether acquired test data is acceptable. The operator tells the test subject which breathing maneuver he must follow for a desired test. The computer stores the test results and the operator may then have the measurement test results analyzed by the computer, compared with standardized predicted values, and printed on a permanent record. The system is capable of measuring, analyzing and computing values for standard Forced Expiratory Volume, Maximal Voluntary Ventilation, Minute Ventilation and Functional Residual Capacity tests.

16 Claims, 11 Drawing Figures

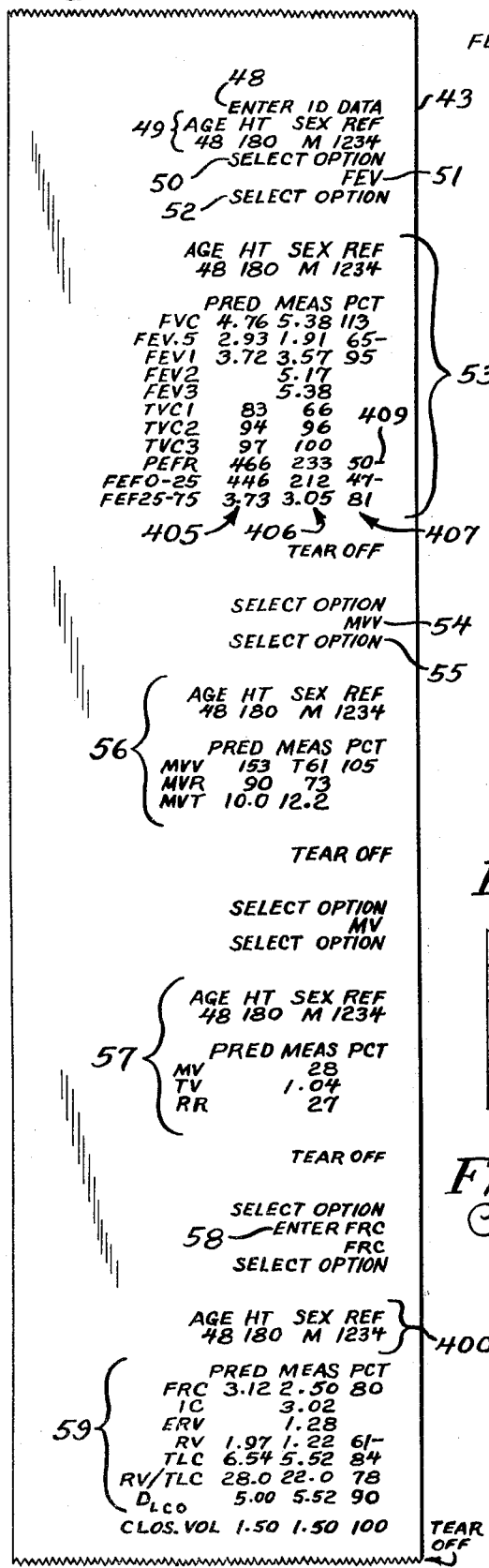
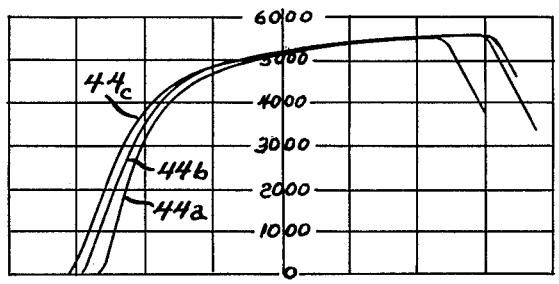
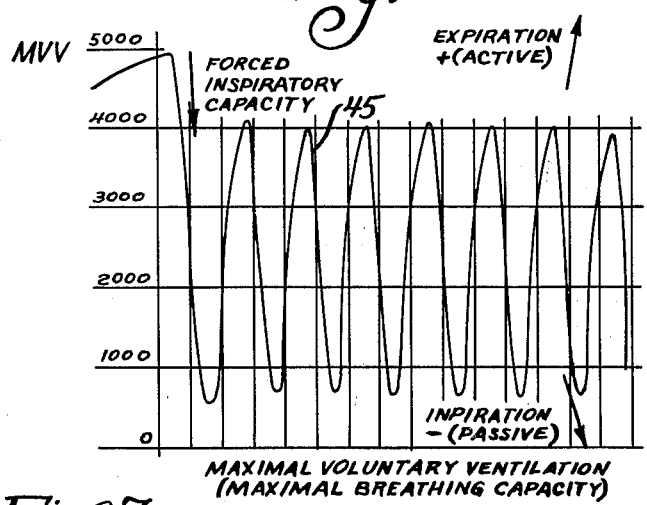
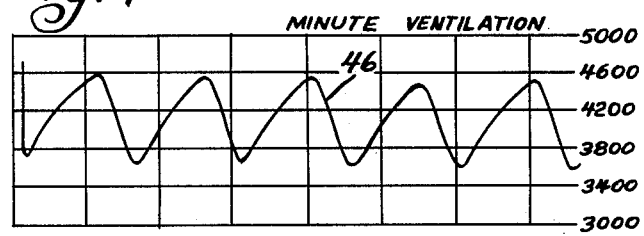
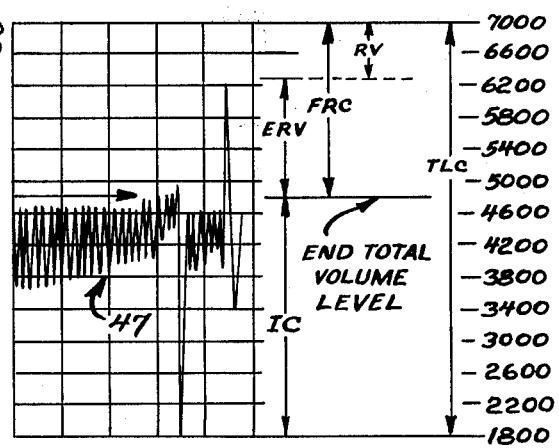

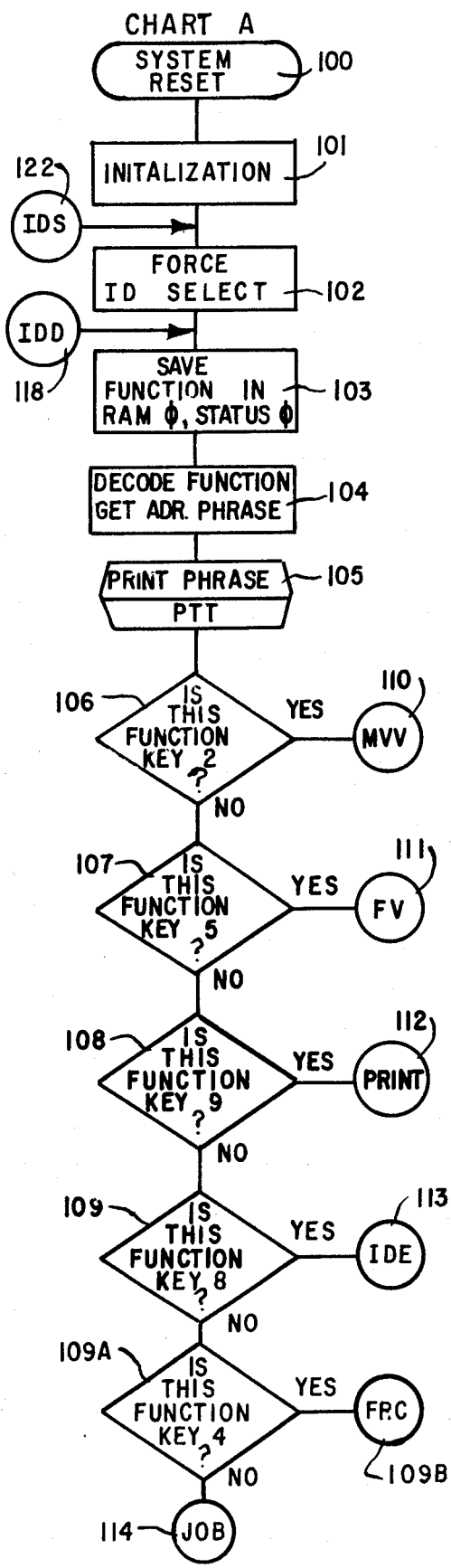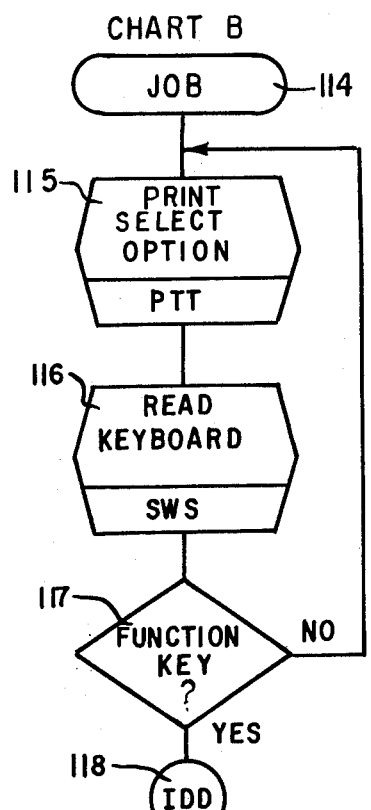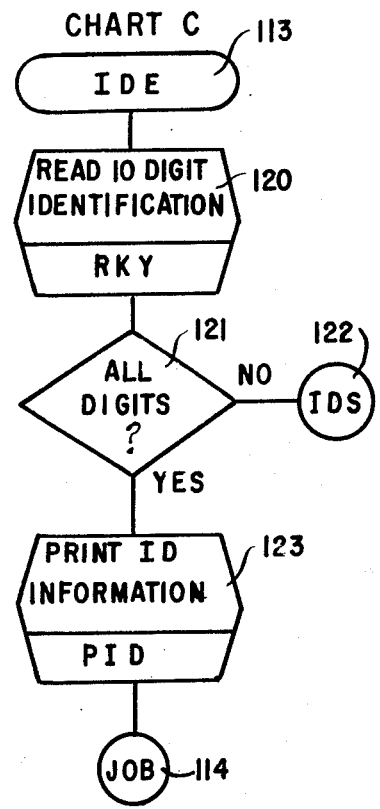

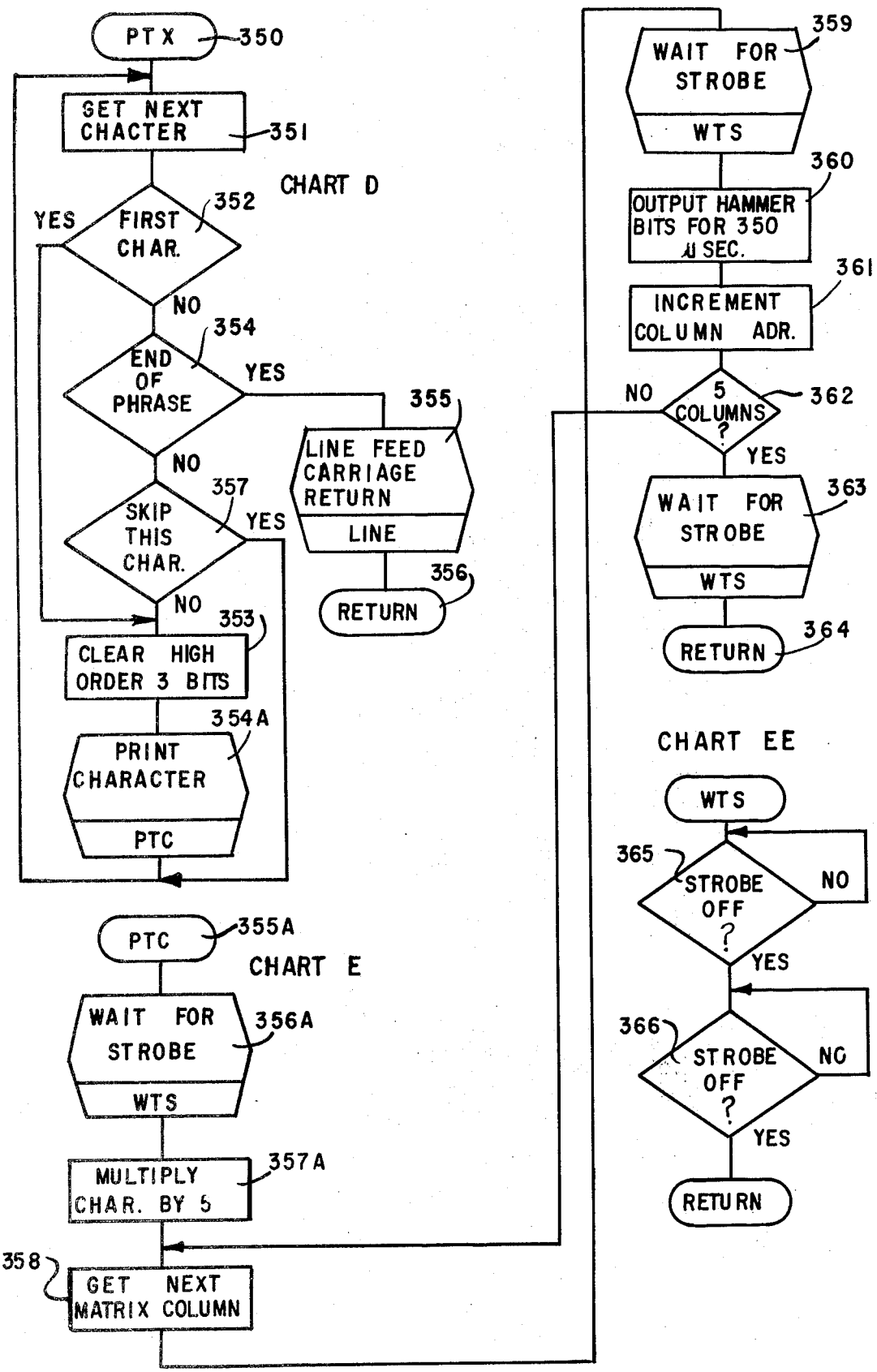

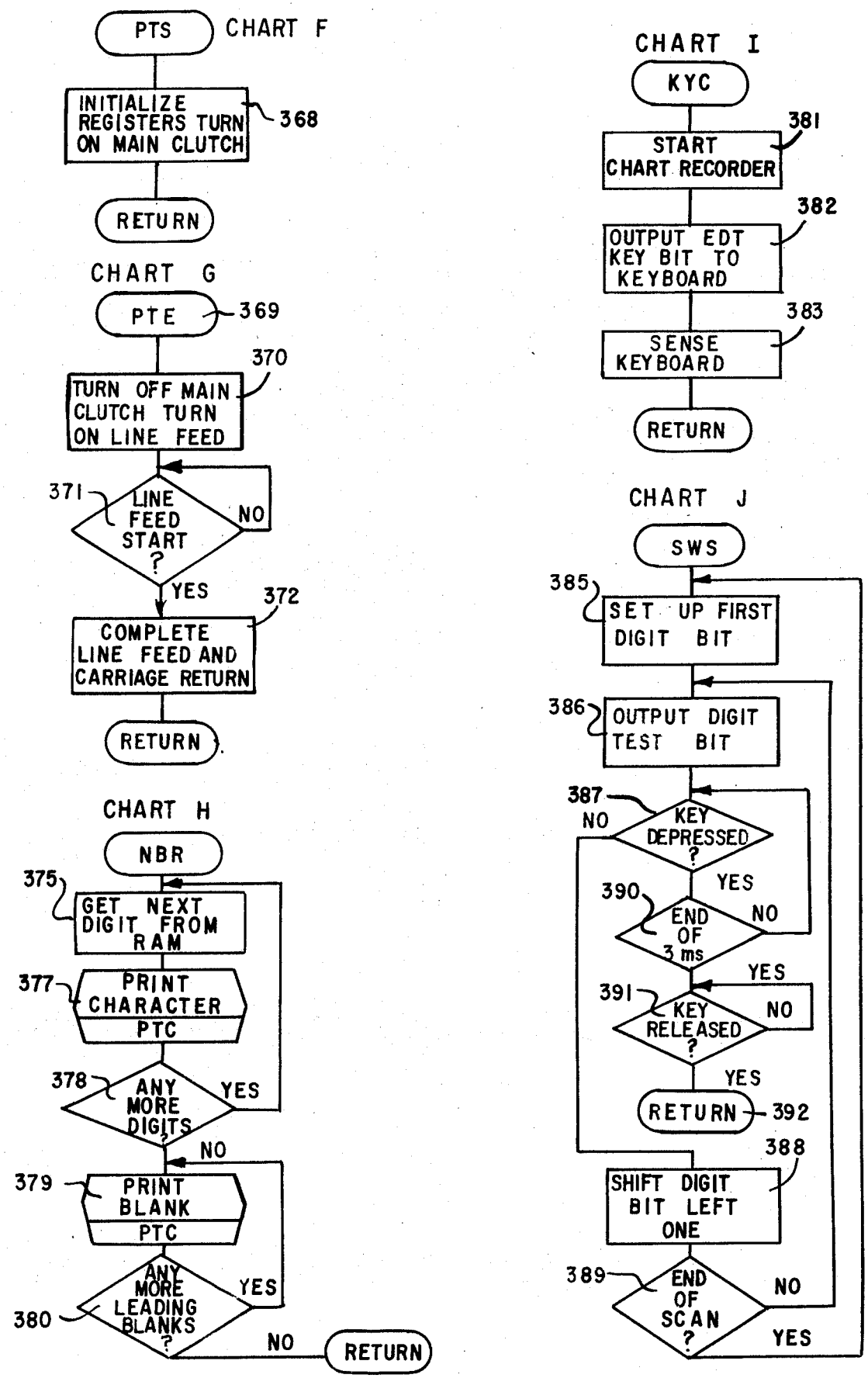

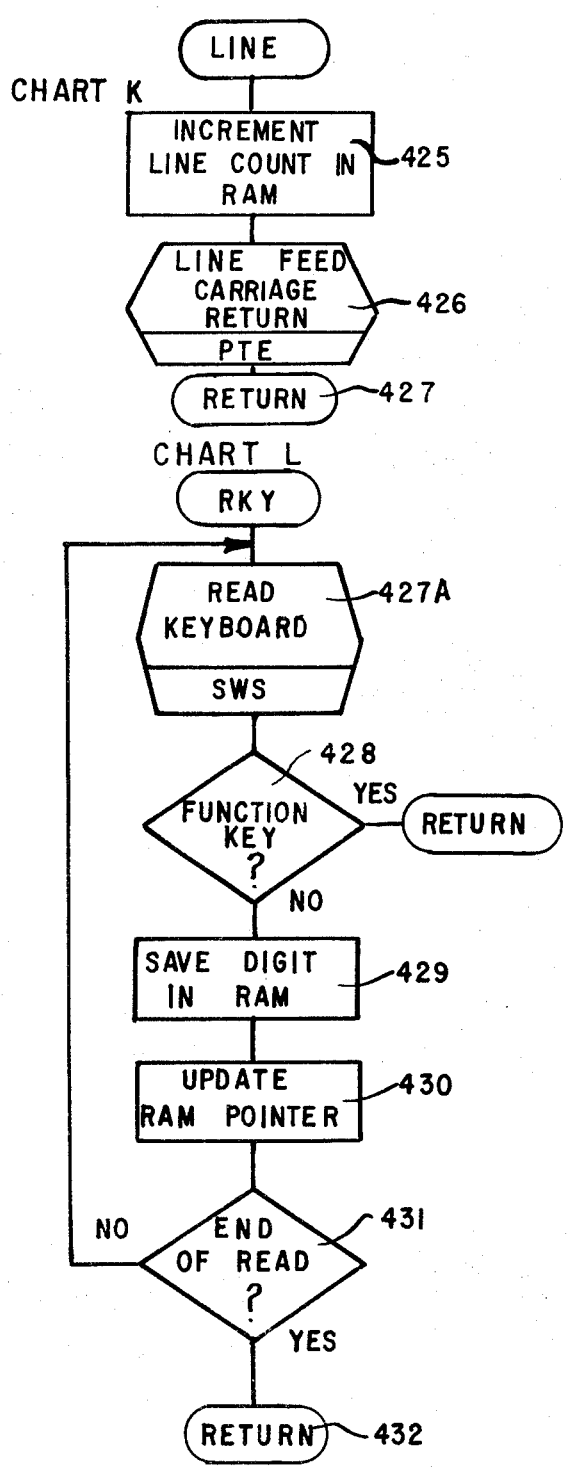
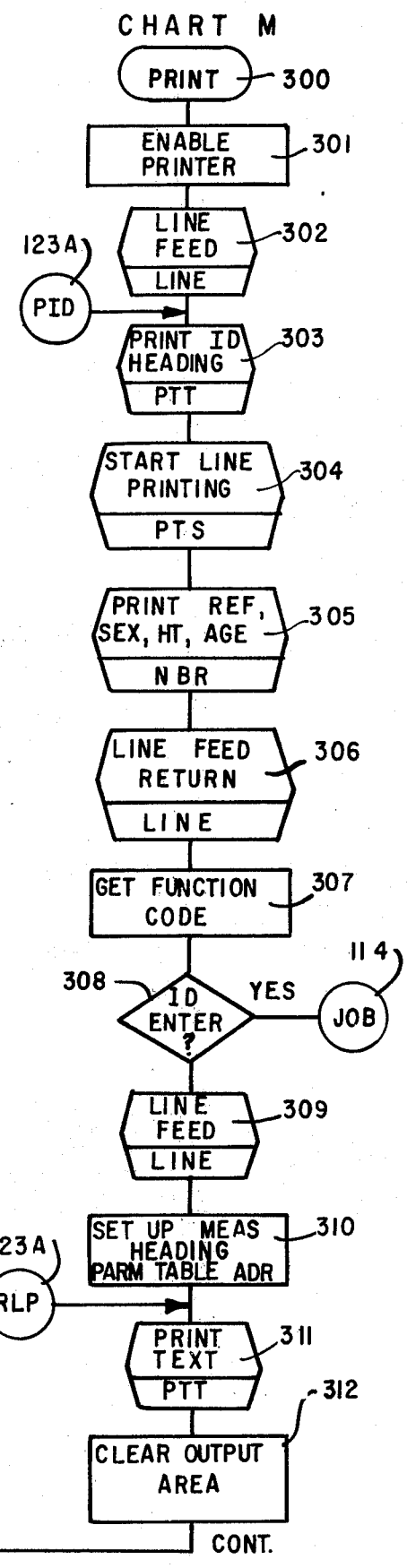

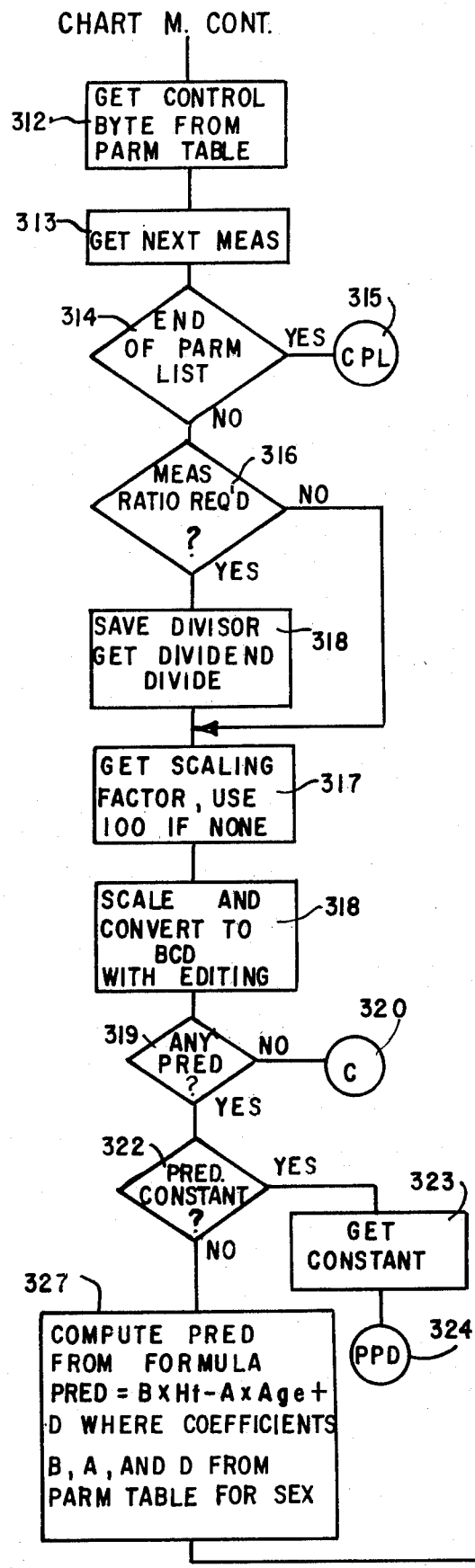
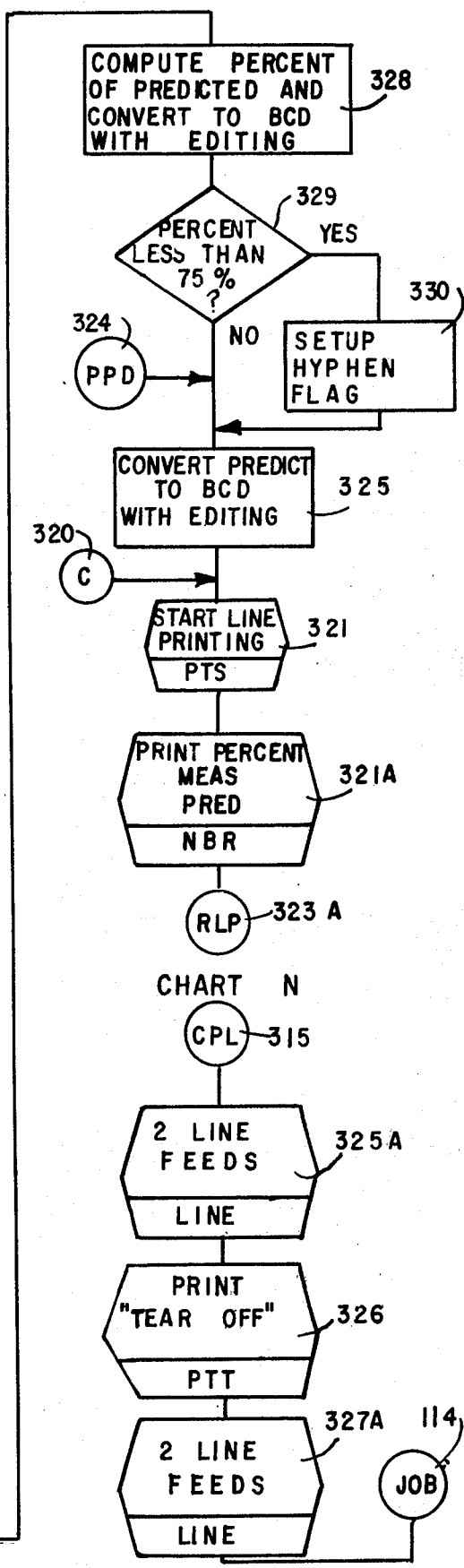

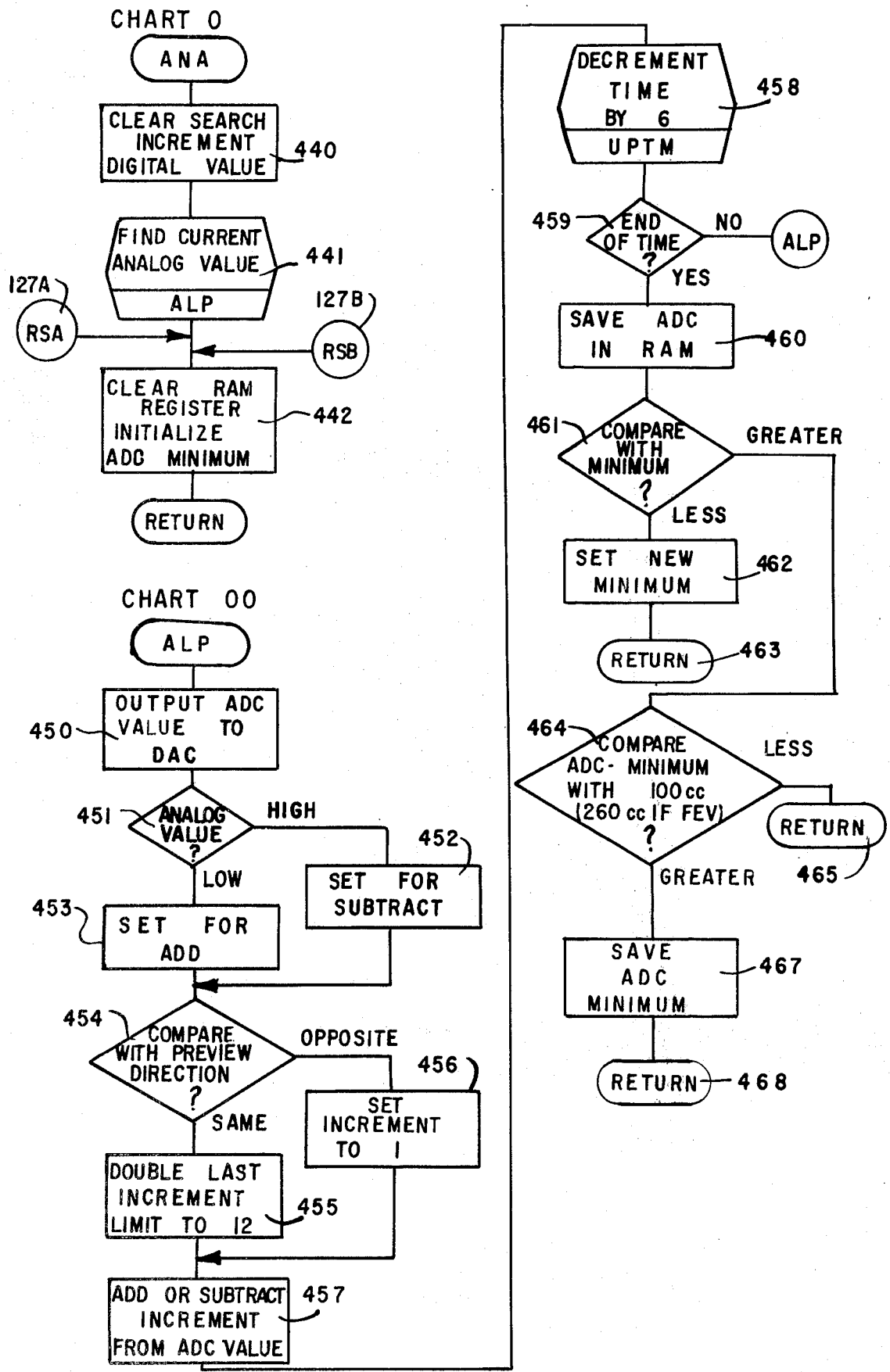

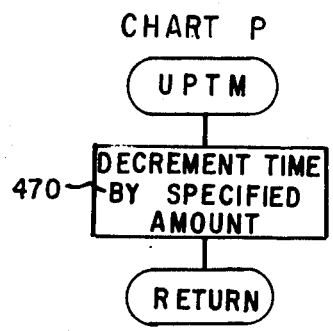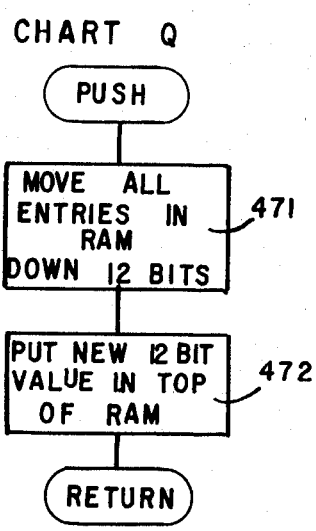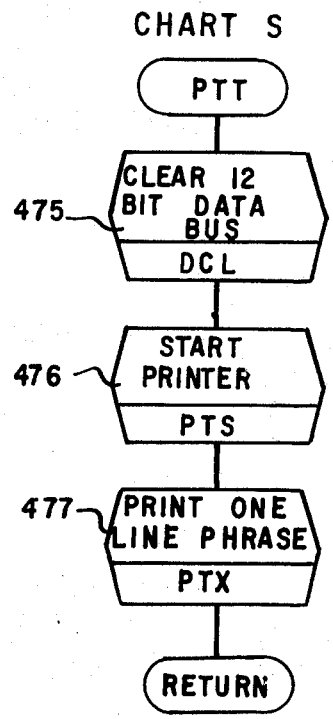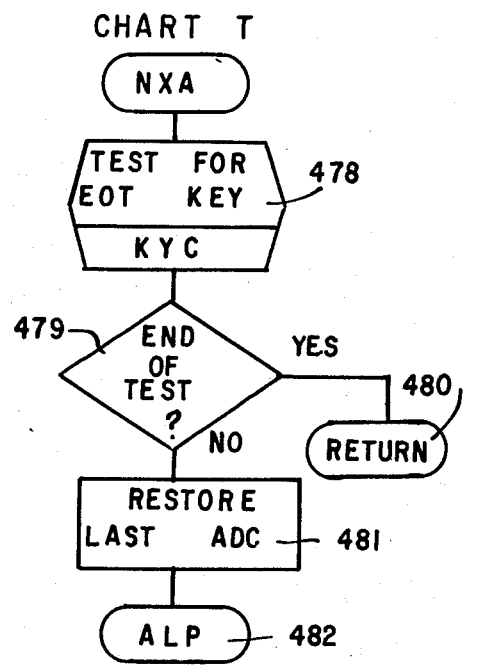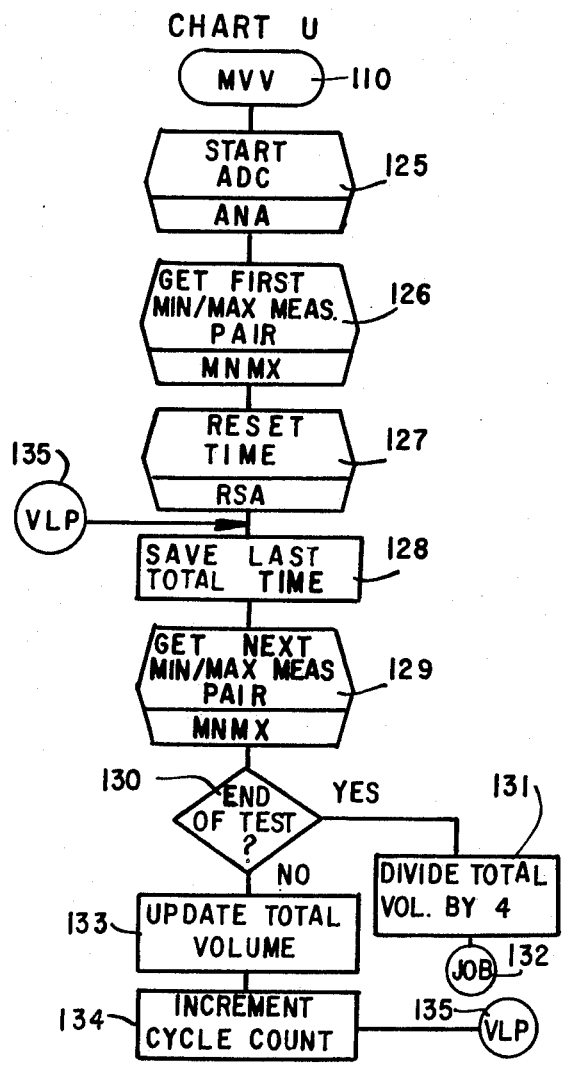

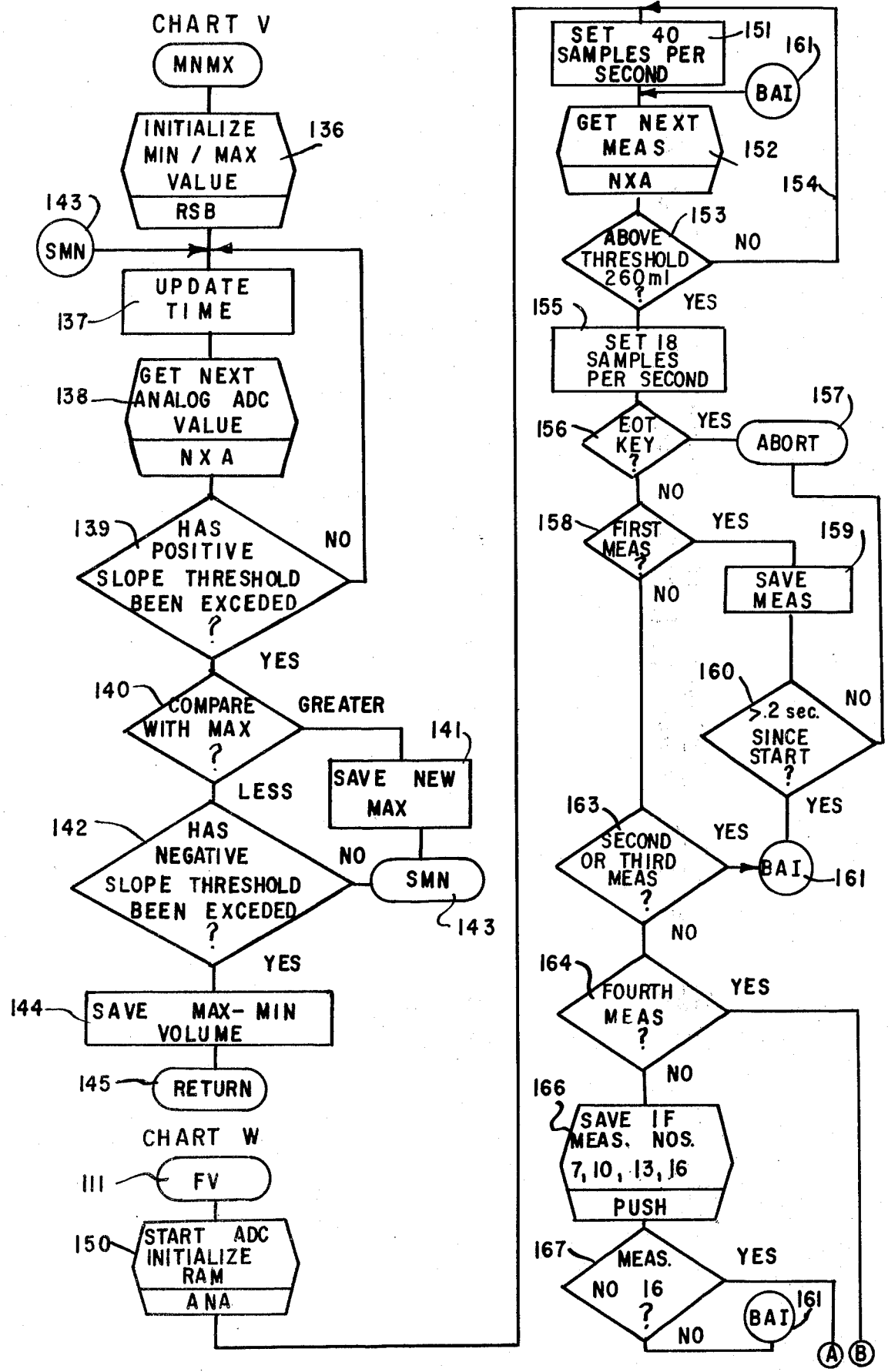

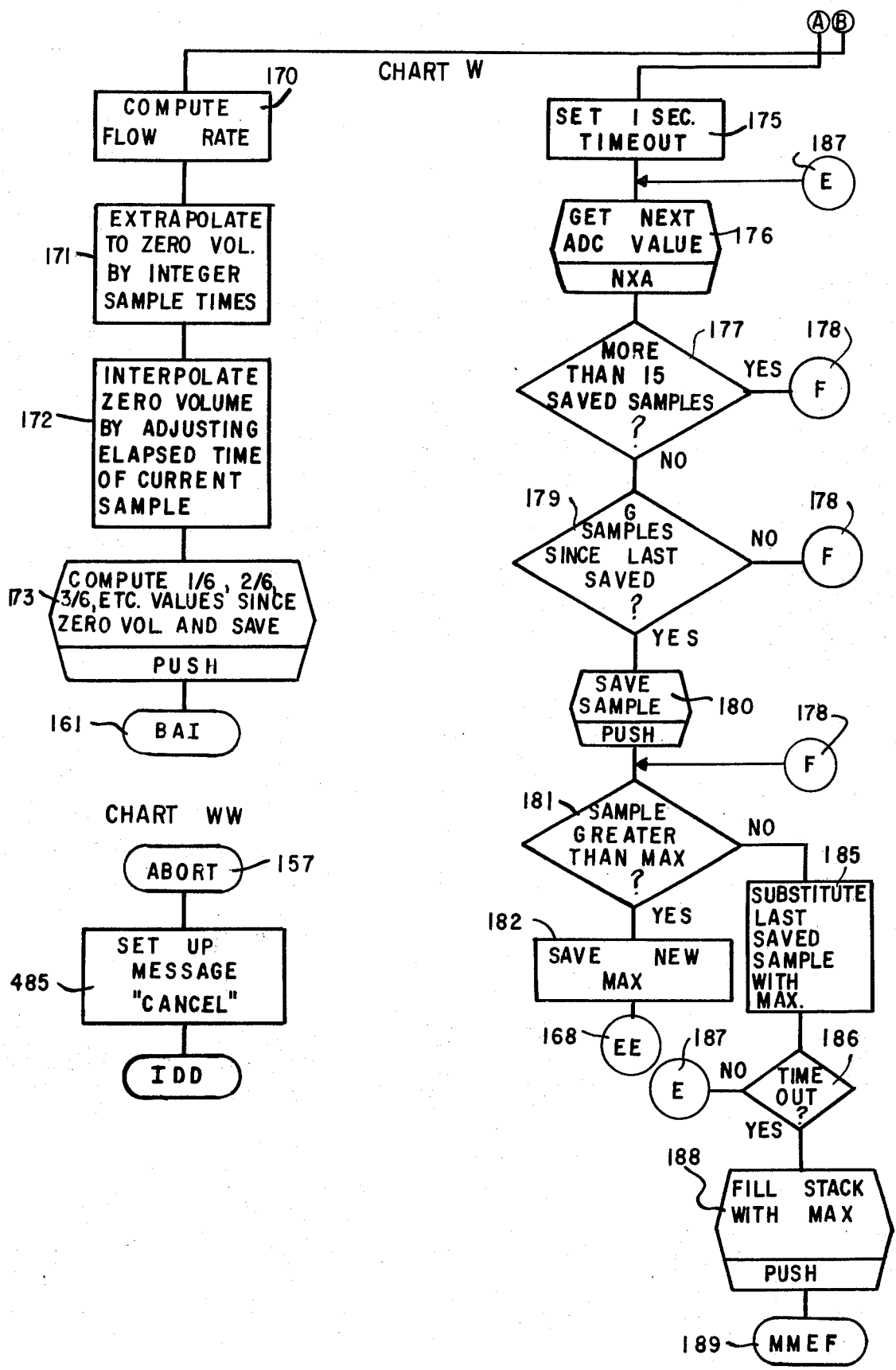

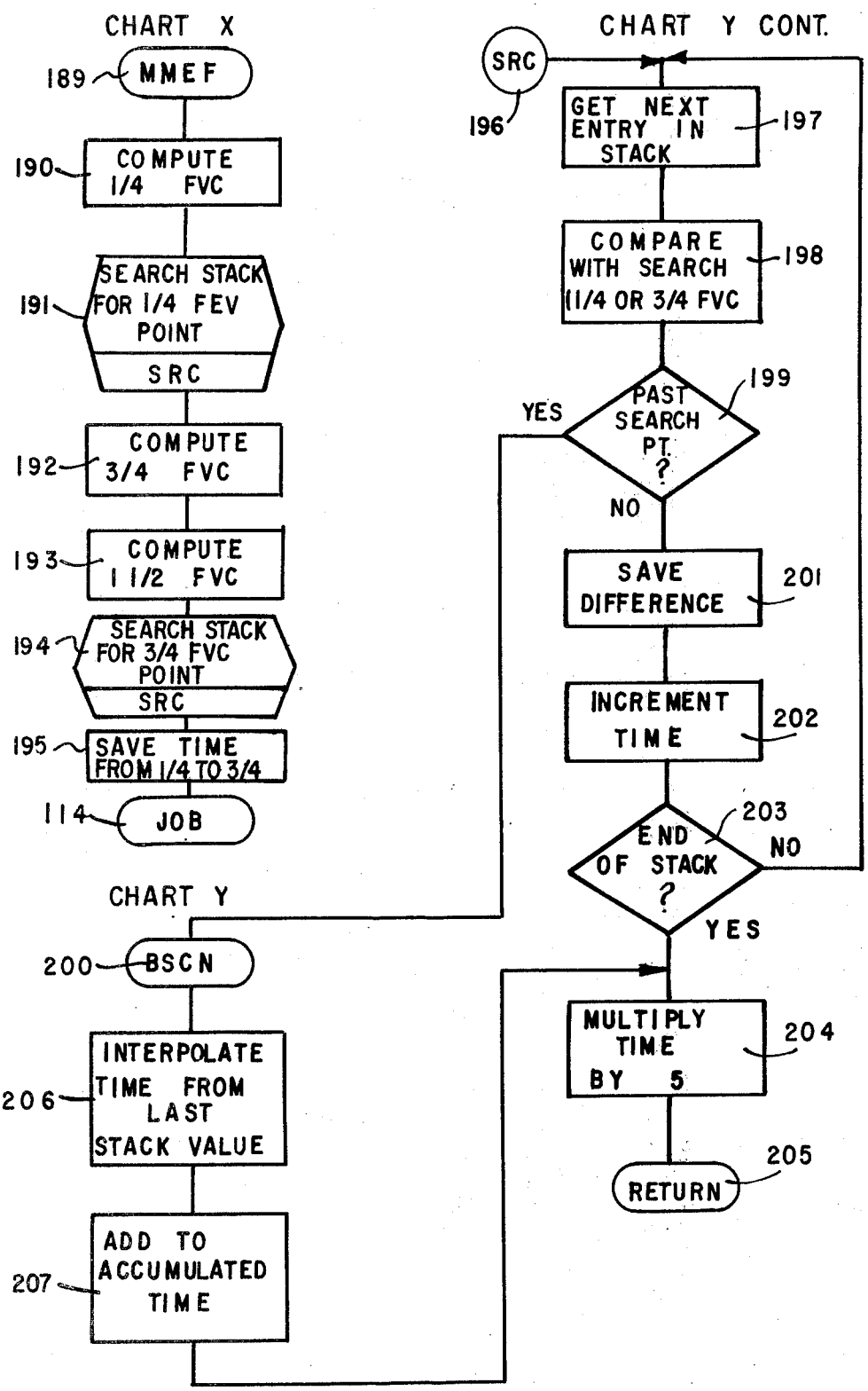

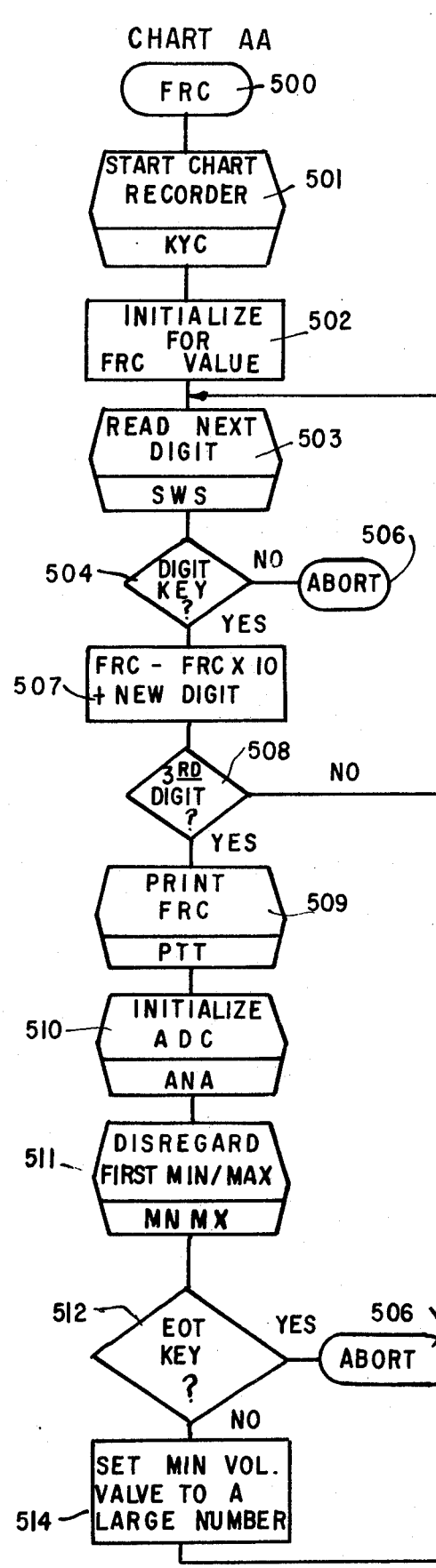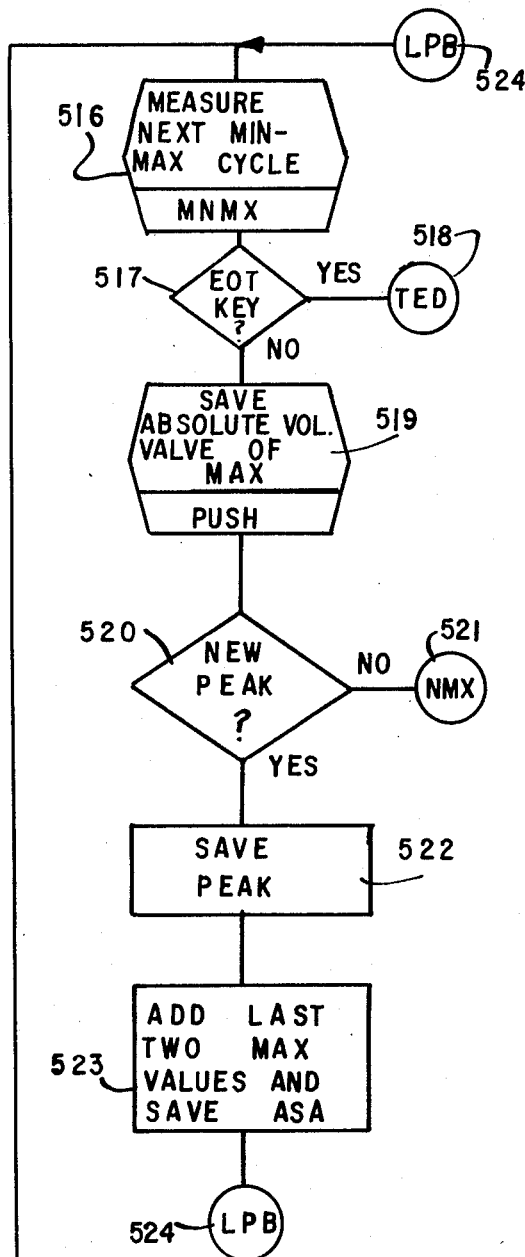

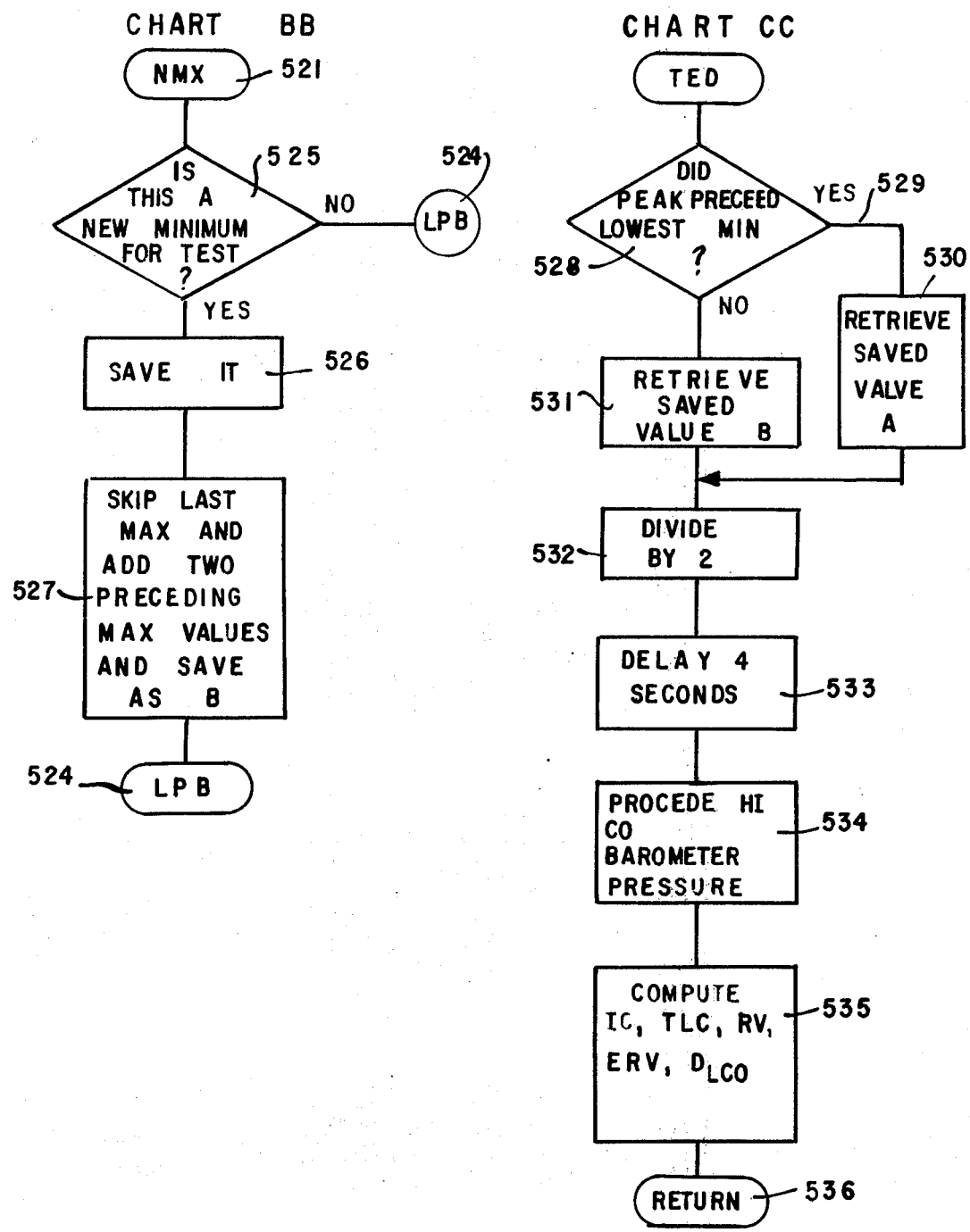

COMPUTERIZED PULMONARY ANALYZER

BACKGROUND AND SUMMARY

The present invention relates to a computerized system for measuring and storing test data for certain pulmonary functions. The system includes a programmable digital computer for analyzing the stored test data and comparing it with standardized predicted values. The test measurements and related predicted values are then printed on a permanent record.

The present system uses a spirometer to generate an electrical signal representative of the volume of air expired or inspired by a person under test who is undergoing a breathing maneuver under instructions of an operator. One such spirometer is disclosed in the Jones U.S. Pat. No. 3,771,512, issued Nov. 13, 1973 for "System for Measuring Timed Forced Expiratory Volume". This spirometer also includes a chart recorder for making a permanent record of the breathing exercise.

In the present system, the analog signal representative of expired breath is fed to a digital computer. The computer controls a matrix printer, and the system also includes a keyboard for the entry of identification data into the system and for enabling the operator to control the system to measure and record the test data for the various tests.

The computer contains a stored program for communicating, through the printer, to the operator what, if anything the operator should be doing. The computer also stores predicted value for each of the various tests, depending upon the age, sex and height of the test subject.

In operation, when the system is first energized, the computer actuates the printer to print the phrase "ENTER ID DATA" which tells the operator to enter identification data for the subject by means of the keyboard. The exact contents of this data will be discussed more fully within. After the identification data is entered, the computer actuates the printer to print the phrase "SELECT OPTION". This tells the operator that he should communicate back to the computer which test is going to be run. The operator or clinician may then take as much time as is required to instruct the test subject regarding the specific breathing maneuver that is required for the selected test. Although others may be added, the present system is designed to accommodate four separate tests: Forced Expiratory Volume (FEV) Test, a Maximal Voluntary Ventilation (MVV) Test, a Minute Ventilation (MV) Test, and a Functional Residual Capacity (FRC) Test. Depending upon which test is desired to be run, the operator then presses a key on the keyboard representative of the selected test. For example, if it is desired to execute the Forced Expiratory Volume Test, then the key labelled "FEV" is depressed by the operator. The computer receives the information and causes the printer to print FEV thereby verifying to the operator which test has been selected and indicating to the operator that he may then proceed with the actual test procedure.

The test subject then executes the breathing maneuver into the spirometer. An analog signal representative of the expired volume is fed to the computer, and the computer samples this analog signal at a predetermined rate and stores the digitalized samples internally until the test is completed.

The computer then analyzes the acquired data in a preliminary fashion and determines whether the test is a valid test. If not, it will notify the operator by printing the phrase "CANCEL". If the computer determines that the storage test data represents a valid test, it prints the phrase SELECT OPTION. At this time, if the operator, upon inspection of the recorded graph, determines that the test data is in fact valid, he may then cause a printout by means of the keyboard, or if the test data is not valid, he may re-select the test, or select and execute a separate test, such as Maximal Voluntary Ventilation.

After the test data has been acquired and stored, and the operator has determined that a test is valid, if the operator causes a print-out, the computer will analyze the test data, compare it with internally stored data representative of standardized predicted values and print out the subject's identification data, followed by the predicted value, measured value and percentage deviation for each test parameter for that particular test.

The computing hardware incorporated in the present invention employs a microminiaturized computer, and circuitry is included for entry of test data into the computer and recall of that data for analysis after entry. The entire computing system, including the printer may be housed in a module about the size of a portable typewriter. Hence, the computer may be easily transported, rendering the system suitable for mass testing in the field—for example in industrial plants.

Further, the specific hardware using certain available components and including other designed connections and circuits renders the system economical. That is, the cost of the entire computing system is about 10–20 percent of the cost that would be required for a general purpose programmable computer adapted to perform similar functions and having similar computational capacity.

One of the major operational features of the present invention is that it eliminates many sources of error that would otherwise be present or possible in a pulmonary analyzer.

In the present system, the analog signal from the spirometer is fed directly to the computer, thereby eliminating possible human error that would otherwise occur in the transfer of data, for example, from a chart or a meter to a permanent record. Hence, one of the features of the present invention is a direct coupling of the measurement signal to the computer which digitalizes it and stores it immediately. It is this stored information which is later used for analysis purposes.

Further, since the computer is programmed to accept only certain sequences during various test maneuvers, it is able to analyze the measurement data according to established criteria to determine whether the test measurement data is valid, and if it is not, to give an indication to an operator through the printer.

Thus, the present invention insures the proper sequence of operations in conducting a test and obtaining test data. It further obviates the need for some of the judgments made by an operator or technician in assessing the validity of a specific test by establishing predetermined criteria which are stored in the computer.

The present invention eliminates another common source of error which occurs in comparing the observed data with prediction tables and prediction computations. The present invention makes comparisons and computations to arrive at predicted normal values, and the deviations of observed data from the predicted normal values in the computer. Further, the computer is capable of being re-programmed to immediately compare prior "baseline" tests.

Still another common source of error which is obviated by the present invention is the transferring of test results to a permanent record. The present system provides an automatic print-out of the subjects identification, test measurements and comparison with predicted normal values on a single compact record—namely, a paper tape which serves as a permanent record, and one which is capable of being photocopied, for example, for transferring test data to a referring physician.

By providing printed test data in digital form, the present system enables an operator to more readily assess whether the characteristics of a particular test indicate that it is valid in light of his experience.

Because the present system is programmable, it can be re-programmed to update data as technology advances, or to include additional tests or test parameters or new predicted normal values, as they become available or are considered more important than what is presently being done. The system can also be modified to process other supplementary test data such as audiometry, cardiac stress testing, etc., which data may be useful in multi-phase testing programs.

Another feature of the invention is the dot matrix printer which is capable of printing the data in different characters, such as Russian, Hebrew, Arabic, etc. at an extremely high speed in comparison with conventional teletype machines.

Still further, the present invention provides data for tests, and displays that data, which has not previously been displayed. For example, mid-expiratory flow rate (FEF 25–75 percent) is considered to be an important indication of sensitivity, and the present invention computes and displays this parameter. Additional capabilities may be added by computing closing volumes, and flow volume loop parameters, among others.

It will thus be appreciated that the present system is an economical, yet extremely reliable and accurate system for analyzing various pulmonary functions. Other features and advantages will be appreciated by persons skilled in the art from the following detailed description of a preferred embodiment accompanied by the attached drawing.

THE DRAWING

FIG. 4 is an illustration of a typical tape printout for the system of FIG. 1;

FIG. 5 is a graph of a typical breathing maneuver for measuring Minute Volume (MV);

FIG. 6 is a graph of a typical breathing maneuver for measuring Maximal Voluntary Ventilation (MVV);

FIG. 7 is a graph of a typical breathing maneuver for measuring Forced Expiratory Volume (FEV);

FIG. 8 is a graph of a typical breathing maneuver for measuring Functional Residual Capacity (FRC);

Table of Flow Charts

| CHART | SUB-ROUTINE | MEMORY ADDRESS | CHART | SUB-ROUTINE |
|---|---|---|---|---|
| A | RESET | | O | ANA |
| B | JOB | | OO | ALP |
| C | IDE | | P | UPTM |
| D | PTX | | Q | PUSH |
| E | PTC | | S | PTT |
| EE | WTS | | T | NXA |
| F | PTS | | U | MVV |
| G | PTE | | V | MNX |
| H | NBR | | W | FV |
| I | KYC | | WW | ABORT |
| J | SWS | | X | MMEF |
| K | LINE | | Z | BSCN, SRC |
| L | RKY | | AA | FRC |
| M | PRINT | | BB | NMX |
| N | CPL | | CC | TED |

DETAILED DESCRIPTION

Figure 1:
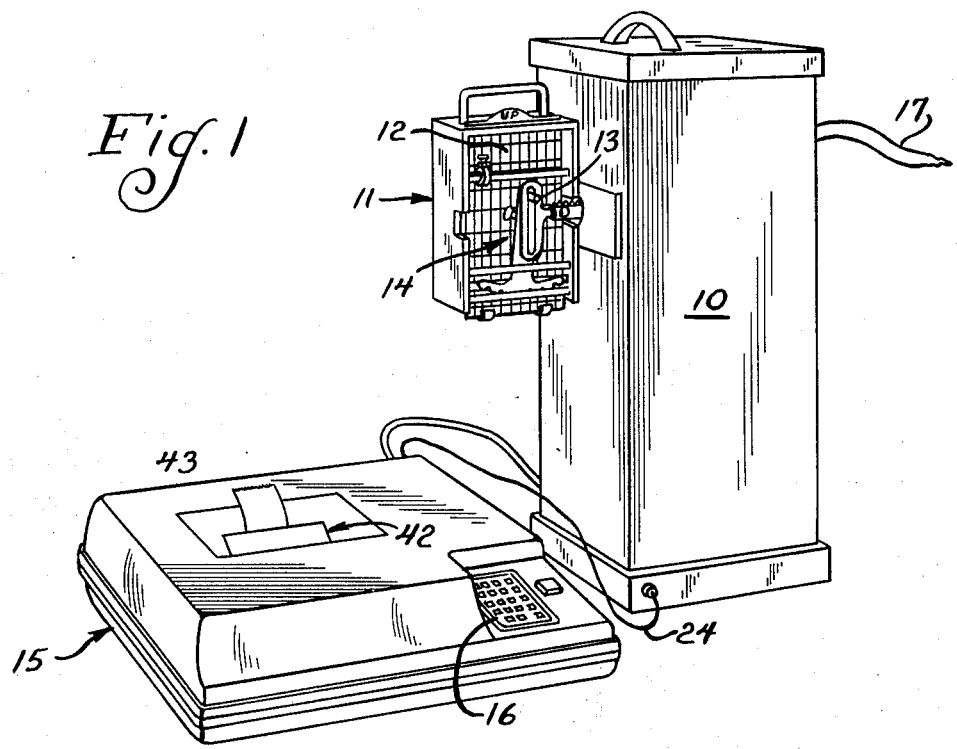
FIG. 1 is a perspective view of a system incorporating the present invention.

Referring first to FIG. 1, reference numeral 10 generally designates a cabinet for a spirometer. To one side of the cabinet 10, there is mounted a chart recorder generally designated 11 and including a chart 12. The chart 12 is mounted so as to be driven in a vertical direction at a constant speed as the test measurement is taken. A synchronous motor is used to drive the chart.

A stylus 13 is mounted to a T-bar linkage generally designated 14 for recording a graph on the chart 12.

A computer module generally designated 15 receives the signal from the spirometer, as will be discussed, and it includes a keyboard generally designated by reference numeral 16.

A subject under test exhales or inspires through a flexible tube 17 which is in fluid communication with a bellows housed within the cabinet 10, but not shown. For example, as a test subject exhales, the air from his lungs will cause the bellows to expand, thereby forcing the T-bar linkage to the left and increasing the magnitude of the signal recorded on the chart 12. In other words, the leftward movement of the T-bar link and stylus is representative of expiratory volume, and the chart 12 is moved downwardly in timed relation with a person's expiration into the instrument so that a curve, such as those shown on FIGS. 5–8 will be generated, the exact shape of the curve depending upon the particular breathing maneuver of the test subject.

Figure 2:
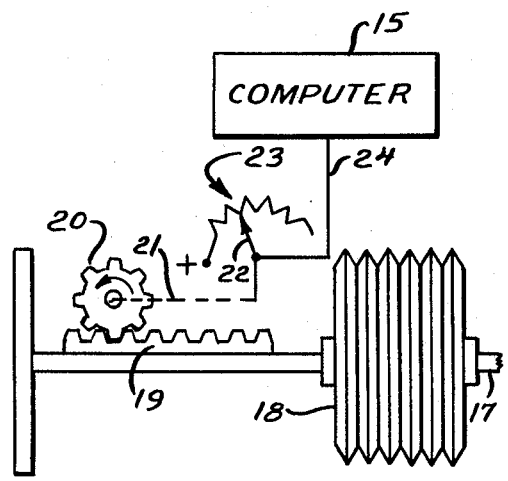
FIG. 2 is a schematic drawing of a T-bar linkage and the electrical transducer for the system of FIG. 1.

Turning now to FIG 2, the base leg of the T-bar link 14 is connected to the movable end of an expandable bellows 18, the other end of which is anchored. The input tube 17, as mentioned, communicates with the interior of the bellows 18. The structure of the T-bar linkage, bellows, mechanism for driving the chart recorder, etc. may be the same as disclosed in U.S. Pat. No. 3,086,515, issued Apr. 23, 1963 which is incorporated herein by reference; and reference is made to that patent for further details.

For purposes of understanding the present invention, a rack gear 19 is connected to the base leg of the T-bar link 14, and it meshes with the teeth of a driven rotary gear 20 which is provided with a shaft 21. The shaft 21 is also connected to the movable wiper arm 22 of a potentiometer 23. Thus, the potentiometer 23 generates an electrical signal proportional to the angular position of the rotary gear 20 which, in turn, is proportional to the horizontal position of the rack 19, and hence, it is proportional to the volume of air in the bellows 18. The analog signal thus generated by the potentiometer 23 which is representative of and proportional to expired breath is coupled by means of a line 24 to the input of the computer 15, shown in functional block form.

KEYBOARD LAYOUT

Figure 3:
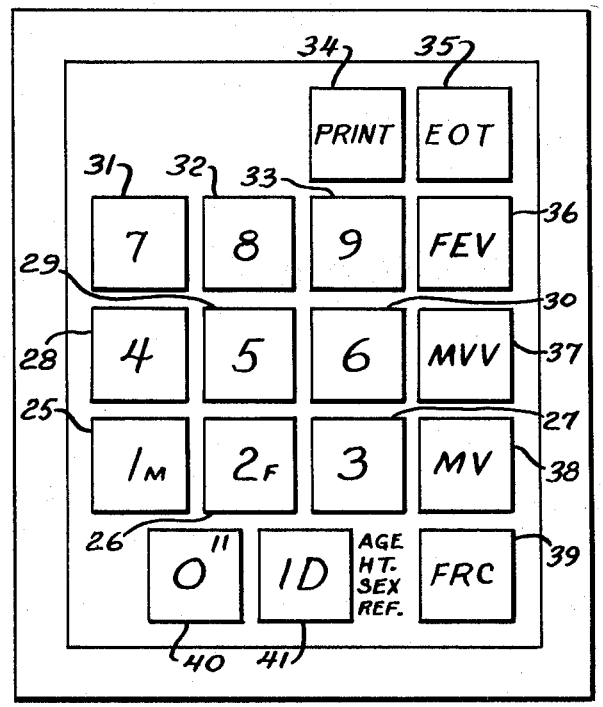
FIG. 3 is a diagrammatic showing of the layout of the keyboard of the system of FIG. 1.

Turning now to FIG. 3, the layout of the keyboard field is shown as including 19 separate keys including keys 25–33 for the digits 1 through 9 respectively in a symmetrical 3 × 3 grid. A "print" key 34 is located above the digit 9 key, and at the right-hand column of the keyboard, five individual keys 35–39 are labelled respectively EOT, FEV, MVV, MV and FRC. These acronyms stand respectively for "End of Test", "Forced Expiratory Volume", "Maximal Voluntary Ventilation", "Minute Ventilation", and "Functional Residual Capacity". The two left-hand keys in the upper row are unused. In the lower row, keys designated 40 and 41 are labelled respectively "O" and "ID". These latter two keys are used respectively for entering the digit O (or inches, as will be explained), and identification data. To the right of the "ID" key 41, there is printed the identification data that is required, including age, height, sex, and a four-digit reference numeral. The sex information, either male (M) or female (F) is entered by depressing, at the required sequence, either switch 25 for male or 26 for female.

GENERAL OPERATION

Before getting into the details of the computer system and the computer programming and operation, it is believed that it would be helpful to have an understanding of the overall system operation first. In this connection, then, reference will be made, in addition to the figures and structure already described, to FIGS. 4 through 8. FIG. 4 represents a typical tape read-out produced by a printer which is generally shown at 42 in FIG. 1 on the computer module 15. The tape is designated 43, and its contents will be described in more detail presently.

FIG. 5 is a graph of three separate Forced Expiratory Volume Curves, designated respectively 44a, 44b and 44c. In the graphs of FIGS. 5–8, the ordinate or vertical coordinate is representative of expired volume, and the abscissa is representative of time. The specific instructions for a given breathing maneuver will be discussed below.

FIG. 6 is a graph produced during execution of the required maneuver for the MVV test, the curve being designated 45. FIG. 7 contains a graph with a curve 46 representative of a typical breathing maneuver for determining MV, and the curve 47 of FIG. 8 is typical of the graph produced during execution of a breathing maneuver for determining FRC.

The spirometer chart recorder 11 is capable of operating at two speeds. One speed moves the chart one-quarter inch per second giving a 32-second chart run since the chart is 8 inches long. In the second speed, which is 1 inch per second, the chart run is 8 seconds long, and this is used primarily for fast speed forced expiratory volume determinations. The printer 42 which is driven by the output of the computer, as will be explained, is preferably a matrix type printer—that is, each character is formed by actuating preselected elements of a rectangular dot matrix. One printer which may be used is Model IPM 130, manufactured by Victor Comptometer of Chicago, Ill. Briefly, this printer is a matrix printer including seven independently driven print hammers which are aligned vertically in a column to form one column of the matrix. The print hammers are then driven in unison horizontally by a carriage drive mechanism to complete the matrix.

As soon as the system is turned on, the computer actuates the printer 42 to print the phrase "ENTER ID DATA", as illustrated at 48 in FIG. 4. This tells the operator that he must enter the required identification data, and for his convenience, the information that is required is printed on the keyboard, as mentioned, and as shown in FIG. 3. The operator need not press the ID key 41 since this key is used to erase data already in the computer, as in the case of a mistake or resetting the system for a new test subject. There are 10 digit locations required for identification data — two digits for age, three for height, one for sex and four for reference. In the case of the height data, the operator has the option of making a three-digit entry in centimeters, such as "180" or a two-digit entry in inches, followed by pressing the button 40 which indicates that the entry is in inches, as illustrated at the upper right-hand corner of the key 40. As already mentioned, for indicating the sex of the subject, the key 25 is pressed for males, and the key 26 for females.

After the 10 identification characters have been entered, the system automatically prints out the data for verification, with suitable headings, as also indicated at the top of FIG. 4 by reference numeral 49. If the operator does not complete this sequence and attempts to run a test, the system will reprint ENTER ID DATA until all required identification data is fed into the computer through the keyboard. As mentioned, if a mistake has been made or data is to be changed or a new entry is being made, the ID button or key 41 is depressed, thereby clearing the portion of the computer which stores the identification data.

Having entered the proper number of characters required for completing identification data, the system verifies what has been entered by printing it, as illustrated, and then prints the phrase SELECT OPTION, as indicated at 50 of FIG. 4 to indicate to the operator that he now has the option of selecting a particular test or, if he desires, erasing and re-entering identification data.

Let it be assumed, for purposes of illustration, that the operator wants to take all four tests, FEV, MVV, MV, and FRC.

FORCED EXPIRATORY VOLUME TEST

If the operator wants to acquire data for an FEV test, the spirometer chart recorder motor is set to the 1-inch position—that is, the rate of feed of the chart 12 in the chart recorder 11 will be 1 inch per second. A chart or graph is placed in the recorder, and the stylus is set to zero. The operator instructs the test subject to inspire all possible air into his lungs, and to hold his breath long enough to put his lips over the mouthpiece which is located, of course, at the input end of the tube 17. The test subject is instructed to forcibly exhale as completely and quickly as possible all of the air within his lungs. Just before the subject exhales, the operator pushes the FEV button 36 on the keyboard, and this activates the computer and the chart recorder motor.

The resulting curve is shown in FIG. 5, which actually shows three separate FEV curves according to customary usage. When the operator depresses the FEV button, the computer causes the printer to print FEV on the tape 43 as indicated at 51, thereby indicating that an FEV test is being run. If the computer, upon preliminary analysis, accepts the data, it prints SELECT OPTION, as indicated at 52, thereby indicating that enough data has been acquired for one test.

If the operator did not push the FEV button soon enough, the computer prints CANCEL and does not accept incoming data. During a test the operator may also cancel the test by depressing the "EOT" button 35, and results in the same action by the computer.

After a set of test data for the FEV test has been acquired, the operator may push the PRINT button 34, and the computer will analyze the stored data and actuate the printer to print out all of the required data, including the identification data indicated at 53 in FIG. 4 for that particular test. If the operator wants a second copy, he simply presses the PRINT button again. If it is desired to take a second FEV test on the same subject, the operator presses the FEV button 36 a second time just before the test subject exhales. After the data has been acquired, the PRINT button 34 is pressed for analysis and read-out. In this second test, the subject's identification data and predicted normal values remain in memory.

Beneath the identification data, the FEV test data is arranged into four columns. The left-hand column identifies the test parameter, the next column gives the predicted normal value for the particular individual being tested, the third column gives the measured values for each parameter for that particular test, and the fourth column gives the percentage relationship between the measured value and the predicted value. If the percentage value is followed by a "hyphen" sign, an abnormality is indiicated.

The following test parameters are measured or computed from the FEV test data: FVC (Forced Vital Capacity), FEV 5 (Forced Expiratory Volume taken one-half second after beginning the test), FEV.1 (Forced Expiratory Volume in 1 second), FEV. 2 (the Forced Expiratory Volume in 2 seconds), and FEV. 3 (the Forced Expiratory Volume in 3 seconds).

In addition, the Timed Vital Capacity is computed as a percentage of Total Forced Vital Capacity for 1 second (TVC1), 2 seconds (TVC2), and 3 seconds (TVC3) after test initiation. Both predicted and measured values are given.

Next, the Peak Expiratory Flow Rate (PEFR) is given, as indicated. Finally, the Forced Expiratory Flow between 0 and 25 per cent of Forced Vital capacity (FEFO-25) and between 25 and 75 per cent of Forced Vital Capacity (FEF25–75) is given.

After the print-out is completed, the computer actuates the printer to print "TEAR OFF" which reminds the operator to remove the permanent record and attach it to the graphic record for the associated data. The print-out is automatically positioned at the tear-off bar to facilitate this.

MAXIMAL VOLUNTARY VENTILATION (MVV)

If the operator then decides to run an MVV test, having already entered the identification data, he sets the chart recorder motor on the spirometer at the one-quarter inch per second speed, and instructs the test subject to breathe in and out as fast and deeply as possible for 10–15 seconds. At the beginning of the breathing exercise, the operator presses the "MVV" button 37, and after the end of the test he pushes the EOT or End of Test Button 35. As mentioned previously, a typical graphic record is shown at 45 of FIG. 6 for the Maximal Voluntary Ventilation test. The operator need not be precise on the time for pressing the MVV and EOT buttons as the computer will defect and compute only for complete breathing cycles.

When the data is entered, the computer prints SELECT OPTION as at 55, and if the operator desires to see a print-out of the analyzed results, he presses the PRINT button on the keyboard, and the information shown at 56 of FIG. 4 is printed, including, again, the identification data followed by the results for the three test parameters. The three test parameters are Maximal Voluntary Ventilation (MVV), Maximal Ventilation Rate (MVR), and Maximal Ventilation Time (MVT), the latter being the duration of the test. Again, for each of the parameters, the system prints the predicted normal value for that particular individual, and on the column immediately next to it the measured result, followed by a percentage value for the MVV. Following the print-out, the printer prints TEAR OFF, again to remind the operator.

After the print-out, the system prints SELECT OPTION again, and the operator may then select, for example, the Minute Ventilation test.

MINUTE VENTILATION TEST (MV)

For this test, the chart recorder motor on the spirometer is set at the one-quarter inch per second speed, and the subject is instructed to breathe normally for 30–60 seconds. The test is initiated when the operator presses the "MV" button 38, and it is terminated when he presses the EOT button 35.

A typical graph is shown at 46 in FIG. 7, and the measurements for the following parameters are computed: Minute Ventilation (MV), Tidal Volume (TV), and Respiration Rate (RR). The Tidal Volume is the difference between averaged peaks and valleys for the curve 46. Print-out is achieved in a manner similar to that already discussed in connection with the other test, and the resulting data is shown at 57 in FIG. 4.

FUNCTIONAL RESIDUAL CAPACITY TEST (FRC)

To perform the FRC test, the one-quarter inch per second speed on the spirometer chart recorder motor is used, and the test subject is instructed to breathe normally for a few cycles, then to exhale maximally, breathe normally for a few cycles and then inhale maximally. The resulting graph is shown on FIG. 8, at 47. Alternately, the test subject may be instructed to breathe normally for a few cycles, then to inhale maximally and then exhale maximally without an intervening normal breathing period.

Referring to the graph of FIG. 8, the breathing pattern moving to the right illustrates the subdivisions of the Total Lung Capacity. These values are important confirmative tests for abnormalities in emphysema, asthma, and other pulmonary diseases. Moving to the right there is a pattern of normal breathing with an arrow indicating the End-Tidal Volume base line. Then, there is a longer downward line; the volume difference represents his Inspiratory Capacity. Then, there are a few normal breaths (to erase the possible phenomena of "air-trapping"), followed by an upward vertical line; the volume difference represents Expiratory Reserve Volume.

If the subject's Functional Residual Capacity can be derived, one can determine his Total Lung Capacity. This FRC can be derived using analysis devices such as disclosed in U.S. Pat. Nos. 3,527,205, 3,527,206, and 3,659,590. It is the total volume residing in the lungs from the level of the End-Tidal Volume, as indicated in FIG. 8.

If this value is entered into the computer when the computer prints "ENTER FRC", the computer determines the End-Tidal base line, Inspiratory Capacity (IC) and Expiratory Reserve Volumes (FRV). It then subtracts ERV from FRC to derive Residual Volume (RV) and adds IC to FRC to derive Total Lung Capacity (TLC). It also computes and prints the RV/TLC ratio which is the most important value.

Prior to executing the breathing maneuver and acquiring the resulting data, the system prints ENTER FRC as shown at 58 in FIG. 4, telling the operator to use the keyboard to enter the subject's measured FRC. The chart recorder motor is turned on at this time to facilitate using the spirometer with other equipment to measure FRC. A three-digit entry is then made, including an assumed (but not keyed) decimal point such as "2.50" (liters). Starting with the stylus at about mid-volume range, the breathing maneuvers indicated above are executed, the operator having pressed the "FRC" button 39 to initiate the acquisition by the computer system. At the end of the test, the operator presses the EOT buttom 35 to terminate the test.

An operator may then press the PRINT button 34, and the data shown at 59 on the tape is printed out.

The following parameters (see FIG. 8 for graphic definitions) are measured or computed, and the results printed in the section 59: Functional Residual Capacity (FRC), Inspiratory Capacity (IC), Expiratory Reserve Volume (ERV), Residual Volume (RV), Total Lung Capacity (TLC), and the ratio RV/TLC. Predicted normal values are also printed for each of the above parameters except for IC and ERV, as indicated in FIG. 4. As with the previous test print-outs, after the print-out is completed, TEAR OFF is printed, followed by SELECT OPTION.

DIGITAL SUBSYSTEM

Figure 9:
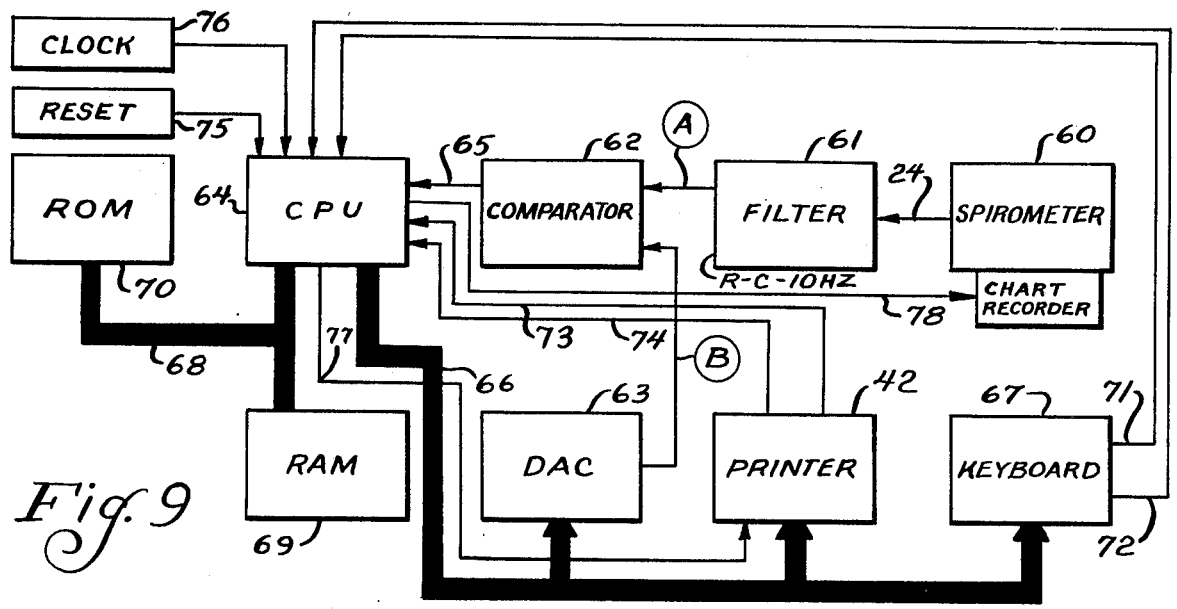
FIG. 9 is a functional block diagram of the system of FIG. 1.

Referring to FIG. 9, reference numeral 60 generally designates a spirometer of the type described above in the Jones U.S. Pat. No. 3,771,512. It generates an analog signal representative of the volume of expired air; and the output lead 24, as previously described, couples this signal to the computer module. This analog signal is fed to a low pass filter 61 to reduce the effects of mechanical noise, etc., in the spirometer.

The output signal of the filter 61 is fed to one input A of an analog signal comparator 62 which may be a conventional operational amplifier having two inputs and having an output signal of only two levels. The output signal is relatively "high" in voltage if one input signal is greater in magnitude than the other, and it is relatively "low" if the one input signal is smaller than the second. The other input B of the comparator 62 is received from a digital to analog converter circuit 63.

The output of the comparator 62 is fed to the central processing unit 64 along line 65. This output signal is a binary signal level indicative of whether or not the input A to the comparator is relatively high or low as compared to the input B. The system function here is to convert the analog output signal of the filter 61 to a digital signal. If the signal on line 65 into the central processing unit 64 is relatively high, it means that the weighted signal value fed to the input of the digital-to-analog converter 63 (and hence, the analog signal appearing on input B) must be increased until such time as the signal on line 65 becomes relatively low. The reverse is also true. The amount of incremental increase or decrease and the sampling time, etc. are functions of the Central Processor Unit and will be discussed more fully below. However, briefly the digital input to the digital-to-analog converter 63 becomes the converted value of the analog signal on line A when the signals on lines A and B are equal within tolerances. In a sense, the analog representation of the input signal to digital-to-analog converter 63 is "hunting" to be equal to the magnitude of the analog signal on input A of the comparator 62; and when this occurs, the digital input signal to converter 63 is taken to be the digital representation of the input analog signal from the spirometer.

The comparator 62 is a very high gain, open loop amplifier such that the output stage saturates in a relatively high or relatively low voltage state, depending upon the relative magnitudes of the signals on the input leads at any given time.

The filter 61 may be a simple R-C filter having a cutoff frequency in the neighborhood of 20 Hz.

Reference numeral 66 generally designates an External Data Bus having 12 bits, even though only 10 bits are used as an input to the digital-to-analog converter 63 (DAC). The bus 66 communicates the CPU 64 not only with the DAC 63, but also with the matrix printer 42 and the keyboard which is generally designated 67. The External Data Bus 66 is a one-way bus transmitting data from the CPU 64 to the other units in the system.

The system also includes an Internal Data Bus 68 which is a four-bit, time-multiplexed bus communicating the CPU 64 with a Random Access Memory 69 (RAM) and a Read Only Memory 70 (ROM).

Returning for a moment to the keyboard of FIG. 3, the External Data Bus 66 has a separate line for each of the digit keys. Each function key is connected in parallel with an associated digit key as follows: 1-MV, 2-MVV, 4-FRC, 5-FEV, 8-ID, 9-PRINT. Separate lines are supplied for EOT and an internal test function.

The External Data Bus 66 thus communicates individually with the digit keys 24B, as indicated. The digit keys include a separate output line 71 which is coupled back to the CPU 64; similarly, the function keys include a separate output line 72 which is coupled back to the CPU 64.

In operation, the CPU sequentially scans the digit keys and their associated function keys; and if a respective key or button is depressed (i.e., the switch is closed), a corresponding signal is transmitted along the respective output line 71, 72 back to the CPU, thereby indicating, as a function of time, to the CPU which key is actuated. Each key is provided with diode isolation so that a signal on one of the individual lines of External Data Bus 66 is not cross-coupled to the other lines. This system design minimizes the number of lines back to the CPU 64, it being realized that 9 lines are required in either case to control the printer 42 for the model identified above.

There are two signal lines from the printer 42 to the CPU 64. These are identified respectively by reference numerals 73, 74, and they transmit a line-feed strobe pulse and carriage strobe pulse respectively for indicating line feeding and carriage movement by the printer. That is, these pulses tell the CPU when the commanded function is accomplished so that the CPU can remove the driving signal. Seven lines of the External Data Bus 66 communicate directly with the print hammers of printer 42. These print hammers have been previously described. An eighth line of Bus 66 communicates with the carriage drive mechanism in the printer and a ninth line with the line feed mechanism.

The preferred Central Processing Unit is a computer sold under the designation MCS-4, Microcomputer Set, manufactured by Intel Corporation of Santa Clara, Calif. The computer and its operation is disclosed in detail in a user's manual, revision 5, published March, 1974, by Intel Corporation, and further reference may be had to that manual for additional details, if required. In addition to power supplies, the two principal support circuits for the CPU include a reset circuit 75 and a two-phase clock circuit 76. Reference may be made to the above-identified user's manual for suggested clock circuits. The reset circuit 75 is a monostable circuit which generates an output pulse when the power supplies are turned on; and this output pulse lasts for a predetermined time to reset the CPU.

Still referring to FIG. 9, there are two additional control leads from the CPU 64. One of these leads is designated 77, and it is a "PRINTER ENABLE" lead which turns on the printer 72. The second lead, designated 78, is used to actuate the synchronous motor of chart recorder 11 of the spirometer. The purpose of this is to have the operation of the chart recorder 11 under control of the computer. Thus, the timing for the graphs on the recorder is supplied by the computer (i.e., CPU).

Figure 11:
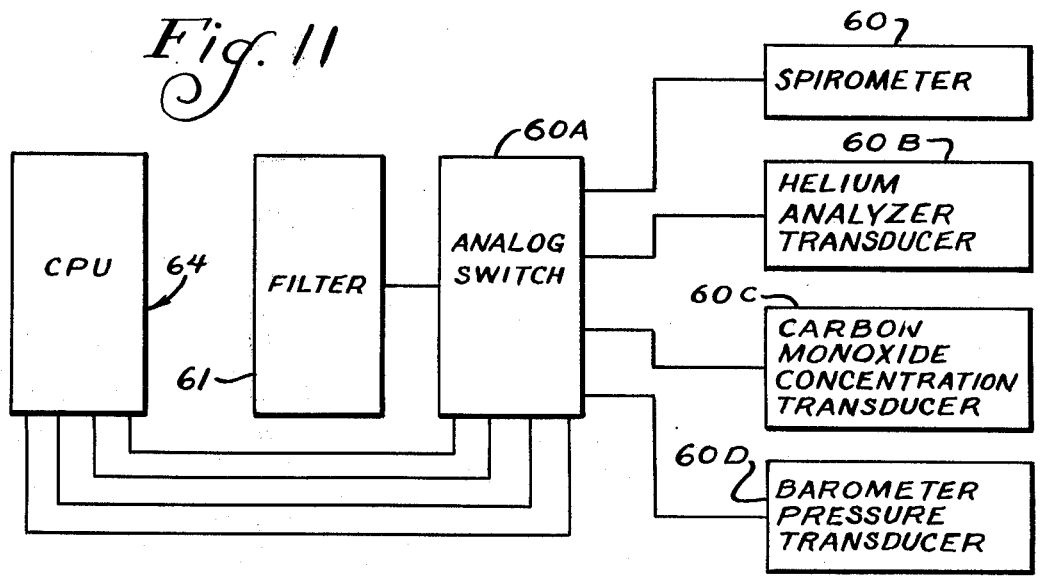
FIG. 11 is a functional block diagram of a modification of the system of FIG. 1 for directly measuring FRC.

The system of FIG. 9 may be used when FRC is measured separately and entered into the computer. Alternatively, the system of FIG. 11 may be used to directly measure FRC. In FIG. 11, only the portions of FIG. 1 that are different are shown, the others would be included though they are not shown. In this embodiment, the output of Spirometer 60 feeds one input of an analog switch 60A which feeds filter 61. A helium analyzer transducer 60B, carbon monoxide contentration transducer 60C, and a barometric pressure transducer have their outputs also connected to the analog switch 60A which selects only one input to feed the filter 61, as controlled by the CPU 64 along four address lines. This modification enables TLC to be computed directly without need for manual entry of FRC. As one method, we can utilize a single breath holding technique, using a standard 10 percent helium, 0.3 percent carbon monoxide, (balance of air) gas mixture.

In this test method a subject exhales all possible volume from his lungs (down to the RV level), then he inspires all possible volume of this standard gas (up to the peak of his IC), and then holds his breath at that peak for 10 seconds.

It has been medically established that the average exhaled helium concentration is diluted directly proportionate to the subject's RV, e.g., if a subject inspired 5 liters volume and exhaled 9 percent helium, this means he had a 10 percent drop in helium concentration; 10 percent of 5 liters indicates an RV of 0.5 liters and a TLC of 5.5 liters.

By use of a second input part to the computer from a carbon monoxide analyzer 60C, and a third input part from an electrical circuit that generates a signal that varies directly with atmospheric pressure 60D we can derive a test called Lung-Diffusing Capacity ($D_{1co}$) in this same breathing maneuver. This test provides one of the earliest indicators for interstitial pulmonary disease as in asbestosis.

Consequently, the computer utilizes these three variables and directly prints out the FRC display of values, followed by a printout of the $D_{1co}$) result, as seen on FIG. 4.

In this manner, since the computer analyzes the change in concentration of helium as it is exhaled, it could easily incorporate tests called "closing Volume" and "Closing Capacity". These are among the newest tests recognized for earliest detection of abnormalities of the lower (terminal airway) lung volumes. Devices are known and commercially available for each of the transducers 60, 60B, 60C and 60D, as well as are analog switches.

DESCRIPTION OF FLOW CHARTS

Turning now to the flow charts—i.e., Charts A–Z, a standard known block notation has been adopted. A square block such as 101 in Chart A is used for a computational or logical routine; a circle such as at 122 is a secondary entry point or such as at 110 an exit point; a horizontally elongated hexagon as at 105 is a subroutine whose "name" or acronym is indicated beneath the horizontal line within the block; and an obround block such as 100 is simply the name of the routine and primary entry point.

Still referring to Chart A, reference numeral 100 indicates System Reset. This is a hardware reset which is accomplished by the reset circuit 75 of FIG. 9 as described above, which resets the CPU 64 when power is turned on. Block 101 indicates the Initialization prior to the main program. These functions are dependent upon the particular computer hardware that is employed, and they correspond to instructions 0 through 4 of the detailed chart listing that is supplied. In block 102, a program indicator is set for the purpose of forcing subsequent entry by the operator of Identification Information (ID) identifying the subject. In block 103, the computer stores information representative of the function key that had been last depressed, or, alternatively, the fact that ID has been forced as indicated in block 102. As will be clear from subsequent discussion, at this point the computer has saved for future use the identification of the function currently being processed. This is then decoded in block 104; and in block 105, there is a subroutine PTT (see Chart S) for printing a suitable phrase associated with the function for instructing the operator to proceed with execution if the selected function. For example, in the case of ID, the phrase "ENTER ID" would be printed, and it would be necessary that he enter the required 10 digits of information identifying the subject, as explained above.

The program then enters a series of decision blocks labelled respectively 106, 107, 108, 109 and 109A. In block 106, it is determined whether either MV Function Key 38 or MVV Function Key 37 had been depressed by the operator. If the answer is "yes", then the subroutine MVV is called via off-page connector 110. This subroutine is shown in Chart U, and is common to both functions MIV and MVV.

If the decision in block 106 is "no", then decision block 107 is entered, and it is determined whether FEV Function Key 36 had been pressed by the operator. If it had been, then the subroutine FV (Forced Expiratory Volume) is entered via connector 111. This subroutine is shown in chart W.

In the next decision block, it is determined whether PRINT Function Key 34 had been depressed; and if so, the subroutine PRINT is entered via connector 112. The subroutine PRINT is shown in chart M.

The next decision block 109 determines whether ID Function Key 41 had been depressed; and if so, subroutine IDE is entered via connector 113. The subroutine IDE is shown in chart C. In decision block 109A, the program determines whether FRC Function Key 39 had been depressed; and if so, subroutine FRC is entered via connector 109B. Finally, if the answer to all of the decision blocks 106–109A is no, then the subroutine JOB is entered via connector 114. Subroutine JOB is illustrated Turning then to Chart B, in the first block 115, the phrase SELECT OPTION is printed. This subroutine is referred to as PTT and is shown on Chart S. This tells the operator that the system is awaiting some further action on his part, and is used in many instances, as will be appreciated from the complete disclosure.

In the next block, 116, a subroutine SWS (see Chart J) awaits depression of a key by the operator. Briefly, it is this subroutine which causes the system to scan the keyboard, as disclosed earlier, and as will be more fully explained below.

In decision block 117, it is determined whether the operator depresses a function key or not. If a function key had been depressed, the program jumps via connector 118 to the corresponding location indicated in chart A. If a function key had not been depressed, the system interprets this as an error, and it loops back to the subroutine indicated in block 115, described above, that is, the JOB subroutine 114 is re-entered.

Turning now to Chart C, the subroutine IDE is entered, it will be recalled from Chart A, via connector 113 when the system had determined in decision block 109 of Chart A that the ID Function Key 41 had been depressed. The program then calls a subroutine RKY, indicated in block 120 and shown in more detail in Chart L for sequentially calling for 10 digits of identification to be entered via the keyboard by the operator. These 10 digits are stored in Random Access Memory in the system. The subroutine RKY will terminate under two conditions: (1) upon the entry of ten sequential digits; and (2) if a key is depressed other than a Digit Key. This is indicated by the decision block 121. If a key other than a Digit Key had been depressed, then the program skips via connector 122 back to the indicated location on Chart A, just prior to block 102. If, on the other hand, all required Digit Keys had been depressed, a subroutine PID is entered in block 123 for printing identification information relative to the subject which had previously been entered by the operator. This subroutine is indicated by the secondary entry point 123A on Chart M—that is, it enters the subroutine PRINT at the indicated point, and more will be said of this in connection with a more complete discussion of chart M.

After the identification information is printed by the printer, the program returns via connector 114 to the subroutine JOB, as already explained in connection with Chart B. As had been indicated in Chart A, if it is determined in block 106 that the MVV Function Key 37 or MV Function key 38 had been depressed, then the subroutine MVV is entered via connector 110.

Turning then to Chart U, a first subroutine ANA is called in block 125. This routine, as indicated in Chart O, initiates the analog-to-digital conversion process, for the spirometer signal. Next, in block 126, the subroutine MNMX is executed. This subroutine is shown in Chart V.

The purpose of the test called for in subroutine MVV is to measure Maximum Voluntary Ventilation. This is a standard rapid breathing maneuver by the subject, as instructed by the operator when he calls for this test. As explained, the subject is instructed to breathe volumes of approximately 50 per cent of his capacity at a frequency (or respiration rate) of about 100 cycles per minute. At this point, the system is operating at a conversion rate of 20 5/6 samples per second. That is, this is the rate at which the analog signal to the comparator circuit 62 is being converted to corresponding digital representation and fed to the computer. The object of the subroutine MNMX is to look for a measure the first minimum volume point and the next occurring maximum volume point that are detected subsequent to calling the subroutine. The first time it is called, it is likely that the data will not be useful because it may have started in the middle of a breathing cycle. The subroutine MNMX also measures elapsed time for that measurement, and in the next subroutine indicated by block 127 and denoted RSA, time is reset to zero and thereby disregarding the first partial breathing cycle. The subroutine RSA is defined by a secondary entry point, denoted at 127A in Chart O.

In the next block 128, the last total time is saved in the event that the test is terminated during the subsequent cycle. Next, the MNMX subroutine is called again in block 129 to measure the next complete breathing cycle (consisting of a minimum and maximum value). Next, in the decision block 130, there is a test to see whether the End of Test Button 35 had been depressed by the operator; and if it had, the total volume is divided by four, for numerical scaling purposes, as indicated by block 131, and the JOB subroutine is entered via connector 132. If it is not the end of test, the total volume is updated in block 133 (that is, incremented by the last volume measurement); and in block 134 the cycle count is incremented—that is, a cumulative count of breathing cycles measured is maintained. Following that, the program loops via connector 135 back to block 128 for saving the last total time and for subsequently obtaining the next breathing cycle measurement, as already described. By saving last total time in this manner, the terminal partial breathing cycle is disregarded in subsequent calculations.

Turning now to Chart V, the subroutine MNMX will be described. It will be recalled that the function of this subroutine is to measure the time and volume between sequential peaks in the Maximum Voluntary Ventilation test. This subroutine performs the same function during the Minute Ventilation test and the Functional Residual Capacity test.

In block 136, a subroutine RSB is entered via connector 127B on Chart O. At this point, accumulated time is not reset. This is the difference between the subroutines RSA and RSB. Next, the program updates accumulated time in block 137—that is, the measurement of total elapsed time. In the next block 138, the next sample of analog voltage is measured. This is accomplished by subroutine NXA, which is shown on Chart T.

In the next decision block 139, there is a determination made as to whether the current sample is at least 100 cc. greater than the minimum measured heretofore in the same cycle. That is, a threshold is set on the positive slope of 100 cc. This is to insure that a transitory minimum is not being measured and that in fact the breathing cycle is proceeding to a maximum (i.e., the positive slope threshold of 100 cc. has been exceeded). If the system determines that this is not the case, then the program loops back to block 137 as previously described.

If, in decision block 139, the system determines that the positive slope threshold has been exceeded, a determination is made in decision block 140 whether the newly-found maximum is greater than or less than the previously stored maximum value. If it is greater than the previously stored maximum value, the program saves that value as the new maximum value in block 141 and proceeds via connector SMN, 143, to the indicated portion on Chart V.

If in block 140 it was determined that the new maximum value is less than the previously stored maximum value, the program proceeds to decision block 142 where it is determined whether the negative slope threshold has been exceeded. The negative slope threshold is similar to the positive slope threshold just discussed, and it determines whether the measured value is at least 100 cc. less than the previously-stored maximum value. If it is, the program is assured that a maximum has in fact been found, and the program then saves the maximum-minimum volume pair in block 144 (this represents a set of values for determining Tidal Volume). If the negative slope threshold is not exceeded in block 142, the program loops back through connector block SMN 143.

After a maximum-minimum pair is found and stored, the program returns via connector 145 to the main program which had called this subroutine.

Returning now to Chart V, the subroutine NXA, which was entered in block 138 updates the minimum value if one is encountered. In the decision block 139, the question asked is whether the positive slope threshold has been exceeded. If not, the program continues to look for new minimums by looping back through block 137 and 138 and recording new minimums if they occur. If, on the other hand, the positive slope threshold value had been exceeded, the program begins to look for a maximum; and in block 140 the current sample is compared with the previously recorded maximum value.

If the current value is greater than that previously recorded, the new value is saved as a current maximum in block 141. If the current value is less than the last recorded maximum value for that cycle, the program determines in decision block 142 whether the negative slope threshold value has been passed. If it has not been passed, a new sample is taken via connector 143 which re-enters the loop just prior to block 137. If the negative slope threshold value had been passed, then the program takes the difference between the maximum and minum volumes and saves that quantity in block 144, and this is recorded as the Tidal Volume or volume for that particular cycle, and it is that value which is used to update the total volume in previously described block 133 of Chart U. Next, the program returns via connector 145 to wherever it was called from, for example, refer to blocks 126 and 129.

Referring to both Charts U and V, in block 137, the program is updating elapsed time since the beginning of the test, but it is not used, for example, if the test is terminated during the current cycle. In order to determine the total time for the test, then, the time is saved in block 128 at the end of each complete cycle. If the test is terminated prior to the end of a complete cycle, the time stored by block 128 is used as the total elapsed time.

The subroutine for determining Minute Ventilation (MV) is the same as for determining MVV. The test is different only in that the operator, calling for a MV test, instructs the subject to breathe his normal rate, as indicated on FIG. 7. Secondly, as determined in the subroutine PRINT and shown on FIG. 4, the following information is printed out:
1. The liters per minute (Minute Ventilation);
2. The average Tidal Volume (the depth of breathing indicated by TV in FIG. 4);
3. Respiration rate (that is, number of breathing cycles per minute).

What is printed out depends upon whether function MVV or function key MV is depressed, but the measurement subroutine is the same.

FORCED EXPIRATORY VOLUME TEST

Referring back to Chart A, if, in decision block 107 it was determined that Function Key 5 had been depressed, then the system enters the FV subroutine via connector block 111, see Chart W.

Subroutine FV begins in block 150 by initiating the Analog-Digital Conversion Process; and the Random Access Memory is initialized, see subroutine ANA and Chart O. In the next block 151, the sample rate is set at 40 samples per second (i.e., 40 conversions per second). The sampling rate is part of the information fed into the sampling routine, as will be explained further in connection wtih subroutine ANA.

The next portion of the program is concerned with gathering data over the first second of the FEV test. Thus, in block 152, the next measurement is obtained by means of subroutine NXA (Chart T) which is an alternative method of entering the main conversion subprogram ANA (Chart O). Briefly, ANA is used to initialize before starting the Analog-Digital Conversion Process, and NXA is introduced each time another measurement is required in the process, subsequent to the first.

Returning then to Chart W, in decision block 153, the program determines whether the volume in the bellows is above 260 milliliters. This is an arbitrary threshold volume called the "preliminary FEV Threshold "; and it is used to determine whether the test has truly been started. That is, it represents a minimum threshold for initiation of the FEV test. If the threshold has not been observed, then the program loops back via line 154 to obtain another measurement by means of subprogram NXA. If the preliminary measurement threshold for FEV has been observed, the program proceeds to set the sample rate to 18 samples per second in block 155. In other words, while the system is trying to determine whether the start has been initiated, a relatively high sampling rate of 40 samples per second is used; however, during normal test data acquisition, 18 samples per second is used as the sampling rate. Next, a decision is made in decision block 156 whether the End of Test Key had been depressed; and if so, the test is terminated via connector block 157 and subroutine ABORT, Chart WW.

Next, in decision block 158, it is determined whether the incoming measurement is the first measurement since exceeding the preliminary FEV threshold mentioned above. If so, the measurement is saved temporarily in block 159 and subsequently, in decision block 160, it is determined whether a time greater than 0.2 second has elapsed since the start. If more than 0.2 second has elapsed since the start of the test, it is taken as an indication that it is true start—that is, that the operator pressed the FEV key prior to the commencement of expiration by the subject. Conversely, if the threshold has been exceeded within 0.2 second since the depression of the FEV key, this is taken as an indication that the subject had begun to exhale prior to depression of the key, and the test has proceeded to some unknown point on the FEV curve above the preliminary FEV threshold. It is desired to terminate the test in such a case and begin a new test.

In other words, if it is determined in block 160 that the patient had begun to expire prior to the operator's depression of the FEV key, the program proceeds to terminate via connector block 157.

If more than 0.2 second had elapsed since the start of the test and the measurement of the preliminary FEV threshold value (260 ml.), then the program loops back to subroutine NXA in block 152 via connector BAI denoted 161 in the same chart.

Returning now to block 158, if the current measurement is other than the first, but the second or third, as determined in block 163, the program continues to loop back to subroutine NXA via connector block 161.

If the current measurement is the fourth measurement—that is, one-sixth of a second from the first measurement, then the program proceeds to block 170. If, in decision block 164, it is determined that it is not the fourth measurement (indicating that it is some measurement subsequent to the fourth measurement), a subroutine PUSH is entered in block 166 for saving measurements 7, 10, 13 and 16—corresponding to samples taken every one-sixth of a second. Further, in decision block 167, if it is the sixteenth measurement, then the program proceeds to block 175. Otherwise, the program loops back through connector block 161 (BAI) to obtain subsequent measurements according to the subroutine NXA in block 152.

The effect of the portion of the program just discussed is to obtain and store measurement samples at the rate of one-sixth of a second for the first second of the FEV test.

Figure 10:
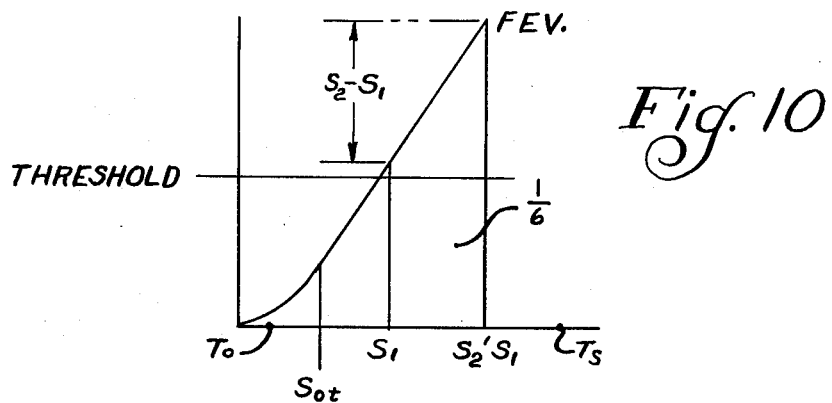
FIG. 10 is a graph illustrating the beginning of a breathing maneuver for determining Forced Expiratory Volume (FEV)

Continuing on with Chart W and referring to FIG. 10, it will be observed that the first measurement (called S1) above the preliminary FEV threshold had been stored while sampling, at a rate of 40 samples per second, and the fourth measurement (S2) had been stored in block 164 while sampling at a rate of 18 samples per second since the first stored measurement such that S2 occurs at one-sixth of a second after S1. The object of the following protion of the program is to extrapolate the preliminary portion of the curve back to zero volume. This is done in two steps. The first phase is to successively subtract from the volume at S1 increments equal to the differential S2 − S1. Then, when the first negative result is obtained, an interpolation is made between the first extrapolated value beneath zero and the one immediately above zero. This procedure eliminates false starts and noise beneath the preliminary FEV threshold.

The flow rate is computed in block 170; and in block 171, an extrapolation is made to zero volume by sample times of one-sixth of a second—that is, by subtracting the differential volume S2 − S1. Next, in block 172, an interpolation is made to zero volume between the two computed samples SO+ and SO−. This extrapolation determines true $T_o$− the begin ning time. At the same time, the program computes the time $T_s$ at which the next sample must be taken such that $T_s$ occurs at a multiple of one-sixth of a second of the newly computed $T_o$.

Again, these values are shown in FIG. 10. Next, in block 173, the subroutine PUSH is entered for a substitution of measurement values at the new values of time (multiples of one-sixth of a second) into the reconstructed measurement curve which had been extrapolated back to zero volume. These measurement values are indicated at S1′, S2′, etc. in FIG. 10.

The program then returns via connector block 161 to the subroutine NXA in block 152 to retrieve the next measurement sample at the newly-computed sample time occurring at a multiple of one-sixth of a second from $T_o$.

At this point, the samples that are stored are those for each sixth of a second subsequent to $T_o$ up to and through five-sixths of a second. Continuing on, a one-second time-out is set in block 175; and it is used in determining whether a new peak is in fact reached during the measurement. In other words, if the program detects a peak (a negative sloping representative of inspiration by the subject), a determination is not made that the detected peak is the maximum value of FEV unless the measurements do not exceed that value within the next second.

The program then proceeds to obtain the next digital measurement value via block 176, using subroutine NXA.

After each subsequent sample, a decision is made in block 177 whether more than 15 samples have been saved, and if so, the program proceeds via connector block 178 to bypass the saving of further measurements, as will be discussed. If no more than 15 samples have been saved, the program proceeds via decision block 179 to determine whether six samples (at the current rate of 18 samples per second) have occurred since the last one had been saved. If the answer is no, the program jumps to connector block 178. If the answer is yes in block 179, that sample measurement is saved in block 180 by the subroutine PUSH. It will thus be observed that measurements are thereafter saved at intervals of one-third of a second, as distinguished from the earlier interval of one-sixth of a second. This remains true for the remainder of the FEV test.

In summary, for the first second of the test, samples of the measurements are saved each one-sixth of a second. For the remainder of the test, sample measurements are saved at each one-third of a second. The last saved measurement, if the test continues, is at 4⅓ seconds.

Proceeding now to decision block 181, even though sample measurements have been stored for the first four seconds of the test, the subject may still be exhaling. Hence, a determination is made as to whether the current sample is greater than the stored maximum, and if it is, that new maximum measurement value is saved in block 182 and the program continues in this loop via connector block 168. If the current sample is less than the stored maximum, the program substitutes the stored maximum for the last measured sample—in other words, since the current measurement is less than the maximum, the program does not permit the current sample to be beneath that maximum and, therefore, substitutes the maximum value that occurred previously for the current measurement value. This is done in block 185.

Continuing on, in block 186, a determination is made as to whether the one second time set in block 175 has elapsed since the last maximum. If not, the program loops back to get the next sample in block 176 via connector block 187, labelled E. If the one-second time has elapsed, values equal to the stored maximum are recorded for all samples remaining in the test by means of subroutine PUSH, in block 188. This, in effect, amounts to a "push-down" stack, and will be discussed later.

At this point, all the test measurements required have been recorded and saved, and the program proceeds via connector block 189 to subroutine MMEF to compute two flow rates.

MAXIMUM MID-EXPIRATORY FLOW (MMEF)

MMEF is the slope of the Forced Expiratory Volume curve from the 25 per cent point to the 75 per cent point (labelled FEF 25–75 in FIG. 4). This routine also computes the slope of the forced expiratory curve between the points zero and 25 per cent (labelled FEFO-25).

Referring to chart X, subroutine is entered by the connector block 189 as previously discussed. In the block 190, a computation is made of a value corresponding to 25 per cent of Forced Vital Capacity. In the next block, 191, a subroutine SCR is entered for searching the stored measurement values to determine the time at which the value computed in block 190 occurred. This is represented by the block 191 which calls the SRC subroutine, Chart E. In the next block, 192, a computation is made of a value corresponding to 75 per cent of Forced Vital Capacity and in block 193, this value is doubled for scaling purposes. Following that, the subroutine SRC is called again in block 194 to search the stack of stored samples to determine the time at which the 75 per cent FVC value occurred.

In block 195, a computation is made of the time difference between the values determined in blocks 191 and 194, representing the time span between 25 and 75 per cent, and this value is stored. The program then returns via connector block 114 to the Job Control routine illustrated on Chart B.

The value of MMEF is the flow rate determined between the 25 and 75 per cent points on the Forced Vital Capacity (i.e., the Forced Expiratory Volume) curve of FIG. 5; and the actual computation of the ratio of volume to time is made in the PRINT subroutine, to be discussed.

Referring now to Chart Y, there is shown a subroutine SRC, previously discussed in connection with the blocks 191 and 194 of Chart X. SRC is entered at 196. The next entry in the memory stack is retrieved in block 197. When the word "stack" is referred to, it means the bank of stored data comprising the stored values of Forced Vital Capacity as previously discussed. These are simply stored in sequential locations of Random Access Memory.

The first time the block 197 is entered, the first value in the stack is retrieved, of course. This value is then compared either with the 25 of 75 per cent value of FVC, depending upon which corresponding time is being sought. This is represented by the block 198. In the decision block 199, a determination is reached whether the search point is passed, and if so, the program jumps to subroutine BSCN (see connector block 200) to interpolate to the proper time, as will be discussed.

If the search point had not been passed, the program, in block 201, saves the difference between the volume being sought and the volume at the sample being considered.

Next, in block 202, the value of time corresponding to the measurement being compared is then incremented. In the next decision block 203, a determination is made as to whether the end of the stack has been reached, and if not, the subroutine loops back to block 197 and repeats itself. If the end of the stack has been reached, the time is multiplied by a factor of five in block 204 for scaling purposes, and the program returns via connector block 205 to the point at which it was called.

Returning to block 199, if it had been determined by the program that the point being searched on the FVC curve had been passed, the program proceeds in block 206 to interpolate the time from the time corresponding to the last stack value of volume to the time corresponding to the exact value being sought, either 25 or 75 per cent of Forced Vital Capacity. In the next block 207, the incremental time determined in block 206 is added to accumulated time to thereby compute a time value corresponding (through interpolation) to the percentage value sought.

In order to accomplish the various functions of the PRINT portion of the program—that is, to print the output report, parameter tables are used to define the contents of each portion of the report.

Referring to Table 15, the allocation of memory will be explained. Certain constants are defined in the first portion of the instruction listing. For example, bits 0–3 define the number of decimal places in the parameter being printed. The next two bits define the type of computation being made, as indicated, the next two bits define whether or not there is a predicted value, and if so, how it is generated, and so on. Memory locations 769 through 777, indicated * by the left-hand column, comprises an index of addresses setting force where the parameter table is located for each of the respective tests for which print-out is required. For example, the parameter table for the FEV test, as indicated in address 774 (that is, the address 769 plus the numerical value of the function key pressed for FEV which is 5), and in this memory location is stored the address for the beginning of the function table for computing FEV. Physically, this begins at instruction 778, as indicated.

Turning now to that instruction, it includes information telling the printer the number of decimal places, the type of computation being made and information on how to compute the predicted value, if any. More particularly, the digits "224" is decimal of a fifteen's complement four-bit code indicating that there are two decimal places to print. The "3" is binary 0011. The first two binary digits comprise bits four and five of the parameter table, discussed above, and the second two bits comprise bits six and seven of the parameter table, already discussed. The subsequent locations in memory contain addresses of RAM memory location for measurements required by the parameter table. Also contained in the table itself are the various constants that may be required for measurement scaling or for computing predicted values according to formula. The last constant in each measurement entry is an address location within the phrase table which contains the associated heading to be printed. The parameter tables are defined in memory locations 768 through 962.

REPORT PRINTING PROGRAM

This program is called by PRINT function key 34, and is diagrammatically entered at the block 300. In the first step, the printer is enabled at block 301. This consists of transmitting an enable pulse to the printer along the line 77, discussed in connection with FIG. 9.

The printer carriage is returned and advanced one line in the block 302 which comprises the subroutine LINE (Chart K). This subroutine includes both a carriage return and a line feed.

In block 303, subroutine PTT prints the identification heading, explained later in connection with Chart S. This is simply a subroutine for printing various phrases.

In the next block, 304, a subroutine PTS (Chart F) is called to start the printing of a line. In the next subroutine, NBR of block 305, a subroutine is called for printing the identification information of the subject, including sex, height, age of the subject and a four-digit reference number. The subroutine is entered for printing each of these identification indicators or headings, and it is shown in more detail on Chart H. Next, in block 306, the subroutine LINE is entered for carriage return and line feed.

In block 307, the function code being executed is retrieved as previously saved in connection with the description of block 103 of Chart A.

Next, the program proceeds to decision block 308 in which it is determined whether the function key being processed is ID function key 41 (for the entry of identification information). If it is, it is an indication that this subroutine had been entered at the secondary entry point 123A or PID (refer to block 123 of Chart C). In other words, in this case, the code of blocks 303–307 is being used merely to print out the identification being entered by the operator in order to verify the same, and not as a heading for the subsequent report. Thus, in the case of processing under ID function key 41, if this is determined in block 308, this portion of the program is exited and the program returns via connector block 114. Otherwise in block 109, subroutine LINE is entered in order to put a line space between the heading and the rest of the report.

In the next block 310, the program sets up the column headings for the report to be printed and, at the same time, retrieves the parameter table associated with the function code being processed. For example, if the parameter being processed is Forced Expiratory Volume, the program retrieves the parameter table for that function.

Next, the text of the report is printed by calling the subroutine PTT, (Chart S) block 311, for printing. Next, in block 312, an output storage area for storing output data to be printed is cleared so that new data may be entered, prior to printing. This simply comprises a preselected memory location serving as buffer storage prior to printing. Continuing on, the program then retrieves the first control byte from the parameter table, as indicated in block 312 and subsequently retrieves the next measurement value in block 313. A decision is made in block 314 whether it is the end of the parameter list, and if so, the program proceeds to subroutine CPL via connector block 315 for clean-up such as line spacing and so forth, as indicated in chart N.

If the parameter list is not ended, the program determines whether a measurement ratio is required in block 316, and if none is required it proceeds down to block 317 to be discussed. If, on the other hand, a measurement ratio is required, such as FEF 25–75, that function is performed in block 318. Thereafter, a required scaling factor is retrieved, and in the event none is specified, the value 100 is used—indicating 100 per cent of the stored measurement.

Thereafter, scaling is performed and the information is converted to binary coded decimal notation with editing such as the deletion of leading zeros, the inclusion of a decimal point, etc. This is indicated by the block 318.

Thereafter, in decision block 319 a determination is made as to whether a predicted value is called for, and if not, the program jumps via connector block 320 to block 321, same chart, to be discussed.

If a predicted value is called for, a determination is made in block 322 as to whether it is a constant, and if so, the constant is retrieved in block 323, and the program proceeds by connector block 324 to block 325, same chart, to be discussed.

If no predicted constant is called for, the program proceeds to block 327 and computes the predicted value from a stored formula of the general forms:

$$B \, s \, HT - A \times AGE + D$$

where coefficients $B$, $A$ and $D$ are retrieved from the parameter table for the particular sex of the subject being tested.

The program then proceeds, in block 328, to compute the per cent of predicted value for the actual measurement, and this information is again converted to binary coded decimal format. Continuing on, in block 329, a determination is made as to whether the actual measurement value is less than 75 per cent of the predicted value. If it is, a hyphen flag is set up for printing in block 330 and the program continues.

Next, in block 325 (note the secondary entry point 324, PPD), the predicted values are converted to binary coded decimal format, as already explained.

In block 321 (note the secondary entry point C, connector block 320), the printing of a line is started by means of the subroutine PTS.

Next, the per cent, measurement and predicted values are printed in block 321A, using the NBR subroutine. At this point, all of the numerical information for one measurement (including predicted value, measurement value, and measurement as a per cent of predicted value) is printed as seen in FIG. 4.

The program now loops back to print the descriptive phrase for the function being processed. This is accomplished by means of a connector block 323A, which re-enters just prior to the block 311 in which the text is printed using the subroutine PTT. The descriptive phrase is then printed, having been retrieved as a part of the parameter table associated with the function under process.

Referring now to FIG. 4, the print-out for the various tests is shown. For each test print-out, the identification verification is shown (e.g., at 400), the instruction to the operator as at 58, or SELECT OPTION, the test being processed at 51, 54, and a separation between the heading and the results is also shown.

The particular printer described prints from right to left mechanically, so that the last information to be printed for the output data is the descriptive term for that line. As indicated for the FEV test, the predicted value for the particular subject is indicated in column 405, the actual measurement value is column 406, and the per cent of predicted value in column 407. Note the hyphen flag 409 where the per cent of predicted value falls below 75 per cent.

Turning now to Chart N, when the subroutine CPL is entered, the program first performs two line feeds in block 325A, using the subroutine LINE.

Next, in block 326A, the phrase TEAR OFF is printed using subroutine PTT. Finally, two line feeds follow in block 327A, and the program returns to job control, Chart B. This completes the report printing phase of the program.

PTX — CHART D

The subroutine PTX is used to print a phrase, and it is most commonly entered from the subroutine PTT. After entry at block 350, the next character is retrieved in block 351, and a determination is made as to whether or not this is the first character of the phrase in block 352. If it is the first character of the phrase, the program jumps to block 353; and if it is not, the determination is made as to whether or not it is the end of a phrase in block 354. This is done by testing the highest order bit in the character. If it is the end of a phrase, the subroutine LINE is called in block 355 for effecting carriage return and line feed, and the subroutine returns to that portion of the program from which it was called in block 356. If, on the other hand, it was determined in block 354 that the character is not the end of a phrase, then a determination is made as to whether or not this character is to be skipped in block 357. This is determined by testing the next higher order bit; and if it is to be skipped, the program loops back to block 351. If this character is not to be skipped, the three highest order bits are cleared from the character in block 353, and the character is printed using subroutine PTC, as indicated in block 354A.

PTC — CHART E

The subroutine PTC is used to print a character, and is entered in various places, represented by the block 355A. The first step in this subroutine is to wait for a strobe pulse from the printer indicating that the carriage has reached the next character position, block 356A calling the subroutine WTS.

In the next block 357, the character is multiplied by five in order to find an address in the character matrix tables stored in read only memory. Each character is made up to five columns which occupy five sequential storage locations in this memory.

In the next block 358 of Chart E, the next matrix column is retrieved from this table, and, again, there is a wait for the carriage strobe pulse in block 359 using the subroutine WTS. There is a strobe pulse for each of the five columns comprising a character, and an extra strobe wait at 356 because there are two columns between characters.

The digital information in the column just received is transmitted to the hammer in block 360 for a duration of 350 microseconds to actuate the print solenoids. Next, the column address register is incremented in block 361, and a determination is made in block 362 as to whether five columns have been printed for this character. If not, the program continues in the loop just described until the five columns are printed. When the columns are printed, another strobe pulse is waited for in block 363, and the subroutine returns to that part of the program from which it was called in block 364.

WTS — CHART EE

As already indicated, this subroutine is used to wait for a strobe pulse from the printer carriage, indicating that it has arrived at the next column for printing. In the first decision block 365, a determination is made as to whether the printer strobe signal is on, and if not, the program loops until one is received. When it occurs, the program waits until it goes off in block 366 and returns. This subroutine includes a double test so that there cannot occur a race condition.

PTS — CHART F

This subroutine is used to start the printing of a new line. In block 368, print control registers are initialized and the main carriage clutch is actuated to initiate carriage movement. It will be observed that the PTC routine, Chart E, assumed that the carriage had been moving. The carriage does not index on the printer disclosed above, but travels continuously.

PTS — CHART G

The PTE subroutine controls the printer in performing a line feed carriage return operation. It is entered at block 369, and in the first block 370, the carriage clutch is de-energized and the line feed clutch is actuated. Next, the system waits for a line feed start signal in decision block 371, the line feed and carriage return are completed in block 372 in accordance with the instructions and specifications of the manufacturer for the particular printer being used. For the particular printer disclosed above, this includes monitoring the return rate, de-energizing the line feed clutch when line feed is completed, and allowing sufficient time to elapse to ensure that the carriage has returned and the printer is ready for the next command.

NBR — Chart H

This subroutine is used to print a numerical field, such as a measurement value or a predicted value. In the first block 375, the next digit is retrieved from the Random Access Memory, and the subroutine PTC is called to print the character retrieved, block 377. Next, a determination is made in decision block 378 as to whether any more digits are required, and if so, the subroutine loops back on itself. If no further digits or characters are required, a leading blank is printed in block 379 using the PTC subroutine, and a determination is made in decision block 380 as to whether any more leading blanks are required. If so, the program loops back to block 379, and if not, the program returns to the location from which the subroutine was called.

KYC—CHART I

This subroutine is used to test for the End of Test Function Key. This key is actuated by the operator and is required to terminate certain tests, such as the MVV.

In the first block 381, the chart recorder is started. This is an auxiliary function of this particular routine. In the next block, the computer transmits a scan signal to the line associated with the EOT key on the keyboard; and in block 383, the keyboard is sensed to determine whether the transmitted signal passed through the closed EOT key, and the result of the tests is then used by whatever portion of the program called this subroutine; and the subroutine returns to the program location from which it was called.

SWS—CHART J

This subroutine is used to scan the keyboard to read individual keys and generate returns when a key is depressed. In the first block 385, the first key is set up, and in block 386 a signal is transmitted from the computer along the particular line associated with that key. In decision block 387, an attempt is made to dispense a return signal (indicating that the key is depressed); and if none is sensed, the digit bit is shifted one to the left in block 388. Thereafter, it is determined whether the scan is ended in block 389, and if it is not, the program moves back on itself to block 386. If the scan is ended, there is a program loop to re-start the scan—in other words, once this subroutine is entered, it will continue scanning until information is sensed. Returning now to decision block 387, if the particular key being sensed is depressed, there is a determination of whether or not 3 milliseconds have elapsed, in decision block 390, since the key was first sensed as being depressed. The 3 millisecond interval is to eliminate the transient effects due to key bounce, if any. After the interval, a determination is made in block 391 as to whether the key has been released, and only if it has does the program return in block 392.

LINE—CHART K

In this subroutine, a line count is maintained in block 425 by incrementing the line count each time the subroutine is entered. Thereafter, subroutine PTE is called in block 426 to implement a line feed, carriage return, and the subroutine returns to the point in the program from which it was called as indicated by the return block 427.

RKY—CHART L

This is a routine for reading and storing a sequence of digits from the input keyboard; and it is used primarily to read and store the 10-digit ID or Identification sequence used to identify the subject under test. In the first block 427, the previously discussed subroutine SWS is used to scan the keyboard; and a determination is made in block 428 as to whether or not a function key is depressed. If so, the subroutine returns to the program at the location from which it was called. If it is not a function key, the digit sensed is stored in Random Access Memory in block 429, and the address register for the Random Access Memory is incremented in block 430.

Next, in decision block 431 a determination is made as to whether or not the end of the required sequence has been reached, and if not, the subroutine loops back on itself to read the next digit. If the end of the sequence has been reached, the subroutine returns to the main program, block 432.

ANA—CHART O

This subroutine is used to initialize the system in order to commence the analog to digital conversion sequence for measurement data. Thus, in block 440, the search increment is set to zero, the current digital value is initialized to zero, also.

The program then proceeds in block 441 to seek the current analog value employing the ALP routine. This is introduced at this point in the program in order to reduce the amount of time for subsequent measurements by approaching the first measurement value. In the next block 442, one of the general registers in the Random Access Memory is cleared for use in temporary storage of intermediate computations. Dpending upon the point at which the subroutine is entered, a different register may be cleared. For example, one general register may be assigned for clearance if entry is made at the secondary point 127A (RSA) or alternatively another register may be cleared if entry is made at the secondary point 127B (RSB). The subroutine then returns to the location in the program from which it was called.

AIP—CHART OO

This routine effects the conversion of the analog values to digital form. In the first block, 450, the current analog value is transmitted along the 10 lines of the 12-bit External Data Bus 66 of FIG. 9 to the digital-to-analog converter 63. In decision block 451 the computer senses the output signal on the line 65 of the comparator 62, and if it is relatively high, in block 452 there will be a set up for a "subtract" operation. If the output of the comparator 62 is relatively low, a set up will be made for an "ADD" operation in block 453.

In block 454, there is a comparison with the high/low sensed in the previous cycle such that if the system determines that it is searching in the same direction (indicating there there has been no cross-over of the actual value) then the last increment is doubled in block 455 (an arbitrary limit of 12 is set). If, on the other hand, it is determined that the last analog value is crossed (i.e., reversed polarity), the increment is set to a value of one in block 456. Following the setting of the increment, the system adds or subtracts the increment as determined respectively in blocks 453 or 452, this function being performed in block 457.

In block 458, the system decrements the time count necessary to get to the next sample by six units of time. A "unit" is one-sixth the amount of absolute time that is consumed by going through one loop of the subroutine ALP. Hence, at this point in the subroutine the program realizes that it is closer to the next sampling time by six units. This is accomplished in the subroutine UPTM.

In the next decision block 459, a determination is made as to whether the end of that particular sampling period has occurred, and if it has not, the program loops back into the subroutine, beginning at block 450. If the sample period has terminated, the current value of digital representation of the input analog signal is saved in the Random Access Memory, block 460. For the frequencies normally encountered, the manner of changing the waited increment for adding or subtracting to the value transmitted to the digital analog converter together with the relatively short time taken to get to this point in the subroutine ALP, for all practical purposes, ensures rapid convergence on the input analog signal between sampling intervals.

In the next block 461, a determination is made as to whether the current value is lower than a previously stored minimum, and if it is, a new minimum is set in block 462 and the program returns via block 463 to the point from which it was called. The setting of a minimum each time one is incurred is a feature which permits automatic zeroing and eliminates a zero setting in the hardware.

If the current value is greater than the previously stored minimum, that value is compared with a quantity equal to the current digital value minus the previously stored minimum with either the 100 cc. slope threshold value required in all tests other than FEV, or in the case of FEV, the preliminary FEV threshold value of 260 cc. as discussed above. If this value is less than the indicated quantity, the program returns via block 465, that comparison having been made in block 464. If the comparison indicates that the current value is greater than the respective threshold, then the quantity representative of the current digital value less the stored minimum is saved in storage, as indicated in block 467, and the program returns to the point from which it was recalled in 468.

UPTM—CHART P

This is the general routine used to decrement time, and as indicated in block 470, time is decremented by a specified amount and the program returns to the point from which it was called.

PUSH—CHART Q

This subroutine implements the "push-down stack" in memory. A particular Random Access Memory section is used for the push-down stack, and whenever there is a new entry, the new entry is placed at the top of the stack and all other entries are moved down 12 bits. The first step is to move the lower entries as indicated in block 471, and then, in block 472, the new 12-bit value is placed at the beginning of the appropriate section of Random Access Memory.

PTT—CHART S

This subroutine sets up the printing of a phrase and then proceeds to the PTX subroutine for commencement of actual printing. In the first block, 475, the 12-bit External Data Bus is cleared; and in block 476, the printer is started using the subroutine PTS. Thereafter, in block 477, a one-line phrase is printed using the subroutine PTX, and the subroutine then returns to the main program at the location from which it was entered.

NXA—CHART T

This is the normal routine used to start the next measurement of an analog value. The first block 478 calls the subroutine KYC (Chart I) for testing whether the End-of-Test Key had been pressed by the operator. A determination is made in block 479, and if it had been pressed, the program returns to the location from which it was called in block 480. If the End-of-Test Key had not been depressed, referring to block 481, the program restores the last reference point for converging on the next sample; and the program then enters the ALP subroutine via connector block 482.

ABORT—CHART WW

In this subroutine, having been entered by connector block 157 in the FV portion of the program (Chart W) the message CANCEL is set up for subsequent printing as a part of the IDE routine to inform the operator that the test has been cancelled. This is represented in block 485 in Chart WW. It is used, for example, if the operator decides to terminate a test prior to completion for whatever reason.

FUNCTIONAL RESIDUAL CAPACITY—CHARTS AA and BB

Referring to FIG. 8, FRC is separately determined by the residual air modules shown in FIG. 1 of the U.S. Pat. No. 3,659,590. The parameter is graphically illustrated in FIG. 2 of that patent. The value in liters is entered by means of the keyboard in the computer system.

Referring then to Chart AA, the FRC test is entered at block 500 by depressing the FRC function key, denoted 39 in FIG. 3. In block 501, the chart recorder is started using subroutine KYC (Chart I), as previously discussed; and in block 502, the FRC value is set to zero. Next, in block 503, the subroutine SWS, discussed above, reads a digit entered by the operator representative of the measured FRC value, as discussed above. A test is made in block 504 to determine whether a digit key had in fact been depressed, and if not, the program is aborted via the connector block 506. If a digit key had been depressed, the accumulated FRC value is computed in block 507 by taking the new digit to be entered and adding it to a value equal to the previously stored FRC times 10—it being observed that the digits representative of FRC are entered in order of descending magnitude, i.e., most significant first.

In block 508, after the third digit has been entered, the system prints the phrase FRC employing subroutine PTT, block 509. Next, the analog digital converter is initialized using the subroutine ANA.

In order to complete the test, the subject has been instructed to proceed through a number of Tidal Volume Cycles as indicated in FIG. 8 at 47; and in block 51, the first minimum point is disregarded using the subroutine MNMX the purpose of which, it will be recalled, is to identify a first min/max pair, defining a breathing cycle.

Next, the program senses in decision block 512 whether the End-of-Test Key has been pressed, and if so, the test is aborted as at the connector block 506. If the test is not ended, the program proceeds to block 514 in which the minimum volume value is set to an arbitrarily large number.

In block 516, again the subroutine MNMX is used to measure the next min/max cycle; and these values are recorded. Again, in block 517, a determination is made as to whether or not the End-of-Test Key has been depressed by the operator, and if so, this is a true End-of-Test and the End-of-Test routine TED is entered via connector block 518. If the End-of-Test Key had not been depressed, in block 519, employing subroutine PUSH, the absolute volume value corresponding to a maximum is saved, as a possible indication that it represents an End Tidal Volume point (ETV of FIG. 8).

This corresponds to saving a value representative of the maximum expiration during this cycle. In the next decision block 520, it is determined whether or not a new peak has been reached for the entire test which may correspond to Voluntary Capacity, VC. If a new peak is not recorded, the program proceeds to the subroutine NMX via the connector block 521 to see whether the minimum recorded for this min/max pair is a new minimum which corresponds to the reference point or maximum Inspiratory Capacity, IC.

If, on the other hand, a new peak is encountered, it is saved in the block 522, and in block 523, the values for the two maximums immediately preceding are added and temporarily saved as a variable labelled A, later to be averaged.

The program then loops via connector block 524 back to retrieve a new min/max pair in the block 516. This sequence will occur until the End-of-Test Key is depressed and the group is exited.

Turning now to chart BB, the connector block 521 is followed by a decision block 525 which determines whether a new minimum has been detected for this particular test; and if it has not been detected, then the program cycles by means of connector block 524 to the block 516 for the measurement of a subsequent min/max pair. If, on the other hand, a new minimum had been detected, it is saved in block 526 as a new minimum.

The program then skips the last maximum value (to discard a portion of the cycle) and adds the two preceding maximum values; and these are saved as a value B. This is accomplished in block 527. The program then proceeds via connector block 524 and loops back to determine a new min/max pair. When the test is ended, referring to Chart CC, a determination is made in block 528 as to whether or not the recorded peak occurred before the recorded minimum. If the peak occurred before the minimum, the program proceeds along line 529 to retrieve the value saved as A in block 530. If the minimum occurred before the peak, then the program retrieves the value saved in B in block 531. In either case, the retrieved value of A or B is divided by two in block 532 and saved as an averaged "End Tidal Volume" point or level (see FIG. 8 for graphic illustrations). From this value, establishing a base line, values are computed for IC, TLC, RV and ERV. These parameters are indicated on FIG. AB, and computed as follows:

Inspiratory Capacity (IC) is computed by subtracting the stored minimum from the averaged value of End Tidal Volume.

Total Lung Capacity (TLC) is computed by adding the previously entered value for FRC to Inspiratory Capacity.

The Residual Volume is computed by first determining the Vital Capacity, (VC). VC is determined by subtracting the minimum value from the peak value. RV is then determined by subtracting VC from TLC.

ERV, Expiratory Reserve Volume is determined by subtracting IC from VC.

The above discussion relates to computing FRC-related parameters after a separate FRC test has been completed and a value entered into the system. With the embodiment of FIG. 11, no separate entry is needed—that is, this system is capable of directly measuring parameters that will enable it to compute FRC, TLC and a variable called Diffusion Lung Capacity for Carbon Monoxide ($D_{LCO}$).

As already disclosed, in order to enable the system to accommodate these direct measurements, an analog switch is added. This analog switch is commercially available and it has four input lines—one to receive the signal from each of the spirometer, helium analyzer transducer, carbon monoxide contraction transducer, and barometric pressure transducer, as shown. The determination of which input line is connected to the filter 61 is set up by four address bits received from the CPU.

In terms of the flow chart, a simple modification is made to chart BB just subsequent to the block 532, which involve first, a delay of 4 seconds to allow the transducers to stabilize in their readings, followed by reading of the separate values of helium concentration (He), carbon monoxide concentration (CO), and barometric pressure. The readings are accomplished by the subroutine ANA, (chart O). In the last block, when the FRC button is pressed, $D_{LCO}$ is computed along with the rest of the parameters already defined. The portion of the program relating to $D_{LCO}$ is described below.

In this alternative method of computing FRC, there would be no manual entry of the value for FRC, consequently blocks 502 through 509 of Chart AA would be deleted. In terms of the program listings, for the embodiment of FIG. 11, the program on the last two pages of lisitings beginning at addresses 2048 through 2289 and continuing on 2304 through 2407 are substituted for 2109 through 2300 of the previous two pages of listings.

PROGRAM LISTING

Turning now to the attached Lists of program instructions, there are 30 such lists, designated L1 through L30. The number in the left-hand column is the associated memory address in which the instruction code (written on the Lists in Fortran computer language) are stored. The address appear, in general, in numerical order, although there are some left out or unused. It will be recalled that the instructions of Lists L28 – L30 inclusive will be substitued for the code at addresses 2109 (list L25 through 2300 (List L26) for the embodiment of FIG. 11 in which FRC is measured directly rather than entered as a pre-measured number into the computer.

In order to relate the flow charts to the program listings, Table I correlates the external labels used in the program listings with the corresponding address for that label. The program listing is broken up into segments or modules of indefinite lengths of related functions. An "external" label is a reference to a label which is defined in another segment of the program. The origins of each module is defined by an origin statement followed by an address, such as "0: = 256".

Where a particular label is found on one of the Flow Charts, that information is given in the "Flow Chart" column.

TABLE I

| EXTERNAL LABEL | ADDRESS | FLOW CHART | EXTERNAL LABEL | ADDRESS | FLOW CHART |
|---|---|---|---|---|---|
| ABORT | 1606 | WW | MPY | 1404 | |
| ADD | 558 | | MVV | 1422 | U |
| ANA | 1280 | | NBR | 679 | H |

TABLE I-continued

| EXTERNAL LABEL | ADDRESS | FLOW CHART | EXTERNAL LABEL | ADDRESS | FLOW CHART |
|---|---|---|---|---|---|
| APTCH | 1751 | | NXA | 1300 | T |
| BPTCH | 1770 | | PID | 1218 | M |
| CLA | 577 | | PRINT | 1206 | M |
| CLR | 581 | | PTC | 416 | E |
| DCL | 588 | | PTE | 473 | G |
| DIV | 603 | | PTS | 464 | F |
| DOUT | 590 | | PTT | 1414 | S |
| FRC | 2048 | | PTX | 243 | B |
| FV | 1536 | W | PUSH | 1386 | Q |
| GPRM | 981 | | RKY | 754 | L |
| IDS | 5 | A | RLP | 1008 | M |
| INCM | 1192 | | RPP | 1005 | |
| IPT | 1000 | | RSA | 1290 | O |
| JOB | 61 | B | RSB | 1292 | O |
| KYC | 724 | I | SET | 563 | |
| LD | 557 | | STC | 555 | |
| LDC | 554 | | STO | 549 | |
| LINE | 739 | K | STT | 582 | |
| LMC | 999 | | SUB | 561 | |
| LMS | 976 | | SWS | 703 | J |
| LMT | 992 | | UPTM | 1378 | P |
| MLT | 1406 | | WTS | 455 | EE |
| MMEF | 1792 | X | XCH | 552 | |
| MMM | 1155 | | | | |
| MNMX | 1495 | V | | | |

```
0:
0:/   JOE CONTROL
0: FIM 14,61   SET REGISTER 14 TO CONSTANT 3
2: SRC 14   SET DEFAULT SRC
3: LDM 13   SET ARITHMETIC PRECISION
4: WR0
5:IDS LDM 9   FORCE ID SELECT
6: XCH 4
7:IDD FIM 0,2   SAVE IM RAM
9: SRC 0   2
10: LD 4
11: CLC
12: DAA
13: JAZ *+2
15: WR0
16: LD 4
17: SRC 14 RESTORE SRC
18: XCH 1   POINT TO FUNCTION TABLES
19:
19: XCH 0
20: FIN 10   GET ROUTINE ADR
21: INC 0
22: FIN 3   GET START PHRASE
23: JMS PTT
25: WMP
26: JIN 10   GO PROCESS
27:PNT JIN PRINT
29:SPP JIN JOE
31:FEV JIN FV   0
33: 0+JOE   (MUST BE AT ADR 33)
34: 0+MV   MV
35: 0+MV   MVV
36: 0+SPP
37: 0+FRC
38: 0+FEV
39: 0+SPP
40: 0+SPP
41: 0+IDE
42: 0+PNT
43: 0+SPP
44: 0+SPP
45:MV JIN MVV
47:FRC JIN FRCR
49: 35   (MUST BE AT ADR 49)
50: 115   MV
51: 113 MVV
52: 111
53: 102   3 ENTER FRC
54: 167 FEV
```

```
55: 111
56: 111
57: 136    ENTER ID DATA
58: 111
59: 111
60: 111
61:JOE FIM 8,149   PRINT SELECT MESSAGE
63: JMS PTT   PRINT, RETURN 4 IN ACC
65: WMP   STOP PRINTER
66: JMS SWS   READ KEYBOARD
68: JNC JOE   LOOP IF NOT FUNCTION KEY
70: JUN ILD
72:IDE FIM 3,57   ID ENTER ROUTINE
74: JMS RKY   READ 10 DIGITS
76: JOC IDS   RESTART NOT DIGIT
78: JUN PID   GO PRINT ID
80:
 0: =85
85:
85:/   PHRASE TABLE
85:/ BIT 0   END OF LST TEXT
85:/     1 SKIP THIS CHAR
85:/     3-7 CHARACTER
85:/ BITS 1,2 NOT TESTED ON 1ST CHAR
85:   22+128   CANCEL
86:   13
87:   24
88:   30
89:   15
90:   24
91:   24+128   FWC
92:   29
93:   14
94:    14+128   TEAR OFF
95: 14
96: 10
97: 0
98: 26
99: 15
100: 18
101: 23
102: 24+128   ENTER FRC
103: 26
104: 14
105: 0
106: 26
107: 13
108: 23
109: 30
110: 13
111:  0+128   BLANK
112: 28+128   MVT
113: 29+64   MVV
114: 26+64   MVR
115: 29   MV
116: 13
117: 24+128   RV/TLC
118: 22
119:
       28
120: 31
121: 29   RV
122: 26+64   RR
123: 26
124: 24+128   FRC
125: 26
126: 14
127: 24+128   IC
128: 23
129: 1+128   ERV1
130: 29   ERV
131: 26
132: 13
133: 24+128   TLC
134: 22
```

```
135: 23
136: 15+128    ENTER ID DATA
137: 28
138: 15
139: 17
140: 0
141: 17
142: 23
143: 0
144: 26
145: 13
146: 28
147: 30
148: 13
149: 30+128    SELECT OPTION
150: 10
151: 22
152: 23
153: 25
154: 10
155: 0
156: 23
157: 24
158: 18
159: 22
160: 18
161: 27
162: 5+128     FEV.5
163: 11
164: 1+64      FEV1
165: 2+64      FEV2
166: 3+64      FEV3
167: 29        FEV
168: 13
169: 14
170: 26+128    PEFR
171: 14
172: 18
173: 25
174: 1+128     TVC1
175: 2+64      TVC2
176: 3+64      TVC3
177: 24
178: 29        TV
179: 23
180: 5+128     FEF0-25
181: 2
182: 12
183: 10
184: 14
185: 18
186: 14
187: 5+128     FEF25-75
188: 7
189: 12
190: 5
191: 2
192: 14
193: 18
194: 14
195: 27+128    MET
196: 18
197: 13
198: 14+128    AGE ... REF
199: 18
200: 26
201: 0
202: 0
203: 19
204: 18
205: 27
206: 0
207: 0
208: 28
209: 21
```

```
210: 0
211: 0
212: 18
213: 20
214: 15
215: 28+128    MEAS PRED PCT
216: 24
217: 25
218: 00
219: 00
220: 27
221: 15
222: 18
223: 13
224: 0
225: 0
226: 17
227: 13
228: 26
229: 25
230:/ PTX    PRINT TEXT ROUTINE, USING PHRASE TABLE
230:LPC RAL    TEST SKIP CHAR
231: JOC LP    ER YES
233:LPB LD 2    CLEAR HIGH 3 BITS
234: RAR
235: TCC
236: XCH 2    2
237: JMS PRC    GO PRINT CHAR
239: STC    RESET FIRST TIME
240:LP ISZ 9,*+3    UPDATE CHAR ADR
242: INC 8
243:PTX LD 9    PRINT TEXT, ENTER WITH CARRY OFF,
244: XCH 1          TEXT ADR IN R8-R9
245: LD 8
246: XCH 0
247: FIN 2    GET NEXT CHARACTER
248: JNC LPB    ER ON FIRST CHAR
250: LD 2    TEST MND
251: RAL
252: JNC LPC    ER NO
254: JIN LINE    CARRIAGE RETURN, LINE FEED
256:
  0: =256
256:
256:/    PRINT CONTROL RON
256:/    CHARACTER TABLE
256: 0    0    BLANK
257: 0
258: 0
259: 0
260: 0
261: 8    NUMBER 1
262: 8
263: 127
264: 24
265: 10
266: 26    NUMBER 2
267: 41
268: 13
269: 13
270: 88
271: 85    NUMBER 3
272: 43
273: 41
274: 9
275: 65
276: 4    NUMBER 4
277: 126
278: 4
279: 4
280: 55
281: 101    NUMBER 5
282: 11
283: 11
284: 11
```

```
285: 83
286: 69     NUMBER 6
287: 41
288: 41
289: 56
290: 102
291: 17     NUMBER 7
292: 3
293: 33
294: 5
295: 73
296: 36     NUMBER 8
297: 41
298: 41
299: 41
300: 36
301: 54     NUMBER 9
302: 97
303: 41
304: 41
305: 26
306: 113    10  NUMBER 0 AND LETTER O
307: 9
308: 9
309: 9
310: 113
311: 0      11  PERIOD
312: 0
313: 72
314: 72
315: 0
316: 32     12  HYPHEN
317: 32
318: 32
319: 32
320: 32
321: 127    13  N
322: 16
323: 34
324: 16
325: 127
326: 1      14  F
327: 33
328: 33
329: 33
330: 127
331: 126    15  A
332: 5
333: 5
334: 5
335: 126
336: 127    16  W
337: 64
338: 36
339: 64
340: 127
341: 33     17  L
342: 80
343: 9
344: 9
345: 127
346: 9      18  E
347: 41
348: 41
349: 41
350: 127
351: 89     19  Y
352: 6
353: 32
354: 6
355: 89
356: 84     20  G
357: 41
358: 9
359: 9
360: 113
```

```
361: 127    21  H
362: 32
363: 32
364: 32
365: 127
366: 8     22  L
367: 8
368: 8
369: 8
370: 127
371: 0     23  I
372: 9
373: 127
374: 9
375: 0
376: 60    24  C
377: 9
378: 9
379: 9
380: 118
381: 18    25  P
382: 33
383: 33
384: 33
385: 127
386: 26    26  R
387: 97
388: 37
389: 33
390: 127
391: 84    27  S
392: 41
393: 41
394: 41
395: 82
396: 1     28  T
397: 1
398: 127
399: 1
400: 1
401: 19    29  V
402: 32
403: 4
404: 64
405: 127
406: 127   30  N
407: 68
408: 32
409: 18
410: 127
411: 1     31  SLASH
412: 18
413: 32
414: 68
415: 8
416:/ LETTERS NOT INCLUDED  BJKQUYZ
416:/    REGISTER USAGE
416:/ R0-1   TEMP ADR OF CHAR MATRIX, ROM ADR E8-11
416:/ R2-3   PRINT CHAR, TEMP MATRIX COL. STORE
416:/ R4     ROM ADR E0-3
416:/ R5     INITIALIZED TO 0 BY PTS
416:/ R6     TEMP ROM ADR FOR E4-7
416:/ R7     LOOP COUNTER
416:/ R14    CONSTANT 3 FOR RAM, ROM3 SRC
416:PTC JMS WTS  PRINT ENTRY, WAIT FOR STROBE
418:PTZ FIM 0,0  INITIALIZE MATRIX ADR
420:    FIM  6,137  /BB  INITIALIZE COUNTERS
422:PNA LD  3   MULTIPLY CHAR BY 5
423:    ADD  1
424:    XCH  1
425:    LD   2
426:    ADD  0
427:    XCH  0
428:    ISZ  6,PNA
430:    INC  6
```

```
431:PNC FIM 2     GET NEXT MATRIX COL
432: JMS WTS      WAIT FOR STROBE
434: SRC 4        OUTPUT B0-3
435: LD 2
436: WRR
437: SRC 6        OUTPUT B4-7
438: LD 3
439: WRR
440: SRC 4
441: LDM 4        SET IDLE COUNT
442:PNE IAC       IDLE TIMING CYCLES
443: JNZ PNE
445: WRR
446: NOP
447: SRC 6
448: WRR
449: SRC 14       RESET SRC
450: ISZ 1,PNG    INCREMENT COL ADR
452: INC 0
453:PNG ISZ 7,PNC LOOP ON 5 COL
455:WTS RDR       WAIT OR STROBE ROUTINE
456: RAL
457: JNC WTS
459:WTX RDR       WAIT FOR NOT STROBE
460: RAL
461: JOC WTX
463: BBL 0
464:PTS LDM 4     PRINT LINE START, SET MAIN CLUTCH
465: FIM 4,32     INITIALIZE R4-5
467:PCM FIM 0,0   OUTPUT PRINT CONTROL ROUTINE
469:PCR SRC 0
470: WRR          WITH CONTENTS OF ACC
471: SRC 14       RESET SRC
472: BBL 0        RETURN
473:PTE LDM 2     END OF LINE ROUTINE
474: JMS PCM      START RETURN, LINE FEED
476:
476:
476:PCA RDR       WAIT FOR LINE FEED START
477: RAL
478: WR3          SET FEED ON IND
479: RAL
480: JNC PCA
482:PCE RDR       WAIT FOR STROBE ON
483: RAL
484: JNC PCD      JUMP NO
486:PCX FIM 6,156 /9C   SET COUNTERS
488: JMS WTX      WAIT FOR STROBE OFF
490:PCY RDR       SENSE STROBE
491: RAL
492: JOC PCC      JUMP ON
494: ISZ 6,PCY    LOOP 16 MS
496:PCC WR3       SAVE FEED STATUS
497: RAR          SETUP CLUTCH/FEED COMMANDS
498: RAR
499: JMS PCM      OUTPUT COMMAND
501:PCD ISZ 0,PCE GO LOOP STROBE ON FOR 16 MS
503: ISZ 1,PCE
505: RD3          TEST FEED CLUTCH STATUS
506: RAL
507: JOC PCX      JUMP STILL ON
509: ISZ 7,PCE    COMPLETE 70 MS WAIT
511: BBL 4        RETURN
512:
  0: =512
512: =512
512: RDM    0   STO
513: JUN XCE
515:   CMC  3   SUB
516: INC 7
517: CMA
518: ADM    6   ADD
519: JUN INC    7   LD
521: SRC 2      9   STC
522: LDM 0      10  LDC
523: XCH 4
```

```
524: XCH 5
525: JUN INC
527: XCH 5      15  XCH
528: RDM
529: XCH 5
530: WRM
531: LD 5
532:XCE SRC 2
533:INC WRM    COMMON LOOP CONTROL
534: SRC 14    RESET SRC
535: JAZ *+3   TEST IF RESULT YET NON ZERO
537: WR3       YES, SET FLAG
538: ISZ 3,*+3  UPDATE PARM ADR.
540: INC 2
541: ISZ 15,IC3   UPDATE ACC ADR, LOOP NOT DONE
543: RAL    SET RESULT POSITIVE/NEGATIVE FLAG
544: RD1    RESTORE R2-R3
545: XCH 2
546: RD2
547: XCH 3
548: BBL 0    RETURN
549:STO LDM 0    0   STORE ENTRY
550: JUN SET
552:XCH LDM 8    EXCHANGE ENTRY
553: XCH 14
554:LDC INC 14   10  LOAD 8 BIT CONSTANT ENTRY
555:STC INC 14    9  STORE 8 BIT CONSTANT ENTRY
556: INC 14
557:LD INC 14    7  LOAD ENTRY
558:ADD INC 14   6  ADD ENTRY
559: INC 14
560: INC 14
561:SUB LDM 3    3  SUBTRACT ENTRY
562: XCH 14
563:SET XCH 7   COMMON SETUP
564: CLB   CLEAR CARRY, NON-ZERO INDICATOR
565: WR3
566: XCH 6   SETUP ROUTINE ADR
567: LD 2    SAVE R2-R3
568: WR1
569: LD 3
570: WR2
571: RD0    SET PRECISION
572: XCH 15
573:IC3 SRC 2    GET NEXT ARGUMENT DIGIT
574: RDM
575: SRC  14  AND SELECT ACC
576: JIN  6   GO TO PROCS ROUTINE
577:CLA RD0   CLEAR PSEUDO ACC ENTRY
578: XCH 3
579: LDM 3
580: XCH 2
581:CLR LDM 0   CLEAR RAM REGISTER ENTRY
582:STT SRC 2   SET RAM REGISTER ENTRY
583: WRM
584: ISZ 3,*-2
586: SRC 14
587: BBL 0
588:DCL JMS CLA    DATA BUS CLEAR ENTRY
590:DOUT FIM 14,61    DATA BUS OUT ENTRY
592: FIM 2,0
594:DA SRC 14   GET NEXT ENTRY
595: RDM
596: SRC 2    OUTPUT
597: WRR
598: INC 2    UP OUT ADR
599: ISZ 15,DA    GO TO NEXT DIGIT
601: SRC 14    RESET AND RETURN
602: BBL 6    2
603:DIV XCH 13  DIVIDE ENTRY
604: FIM 2,59 /3E    SETUP 20 BIT DIVIDEND
606: JMS STO
608: FIM 2,62 /3E
610: JMS CLR
612: LDM 11    SET 20 BIT PRECISION
```

```
613: WR0
614: LDM 14    SET COUNTG6 FOR TWICE X10
615: XCH 5
616: DV1 LDM 7    MULTIPLY ACC BY 10
617:    XCH 4
618: FIM  2,43  /2B
620: JMS STO
622: JMS ADD
624: ISZ 4,*-2
626: ISZ 5,DV1    GO FOR SECOND X10
628: JMS   CLR    CLEAR /2B THRU /2F
630: JMS   STC
632: DV3 FIM  2,40 /2B  SUBTRACT LOOE
634: FIM 6,3
636: JMS SET+8
638: JOC DV6    ER IF COMPLETE
640: DV5 SRC 2
641:    RDM
642:    IAC
643:    WRM
644:    INC 3
645:    JOC DV5
647:    FIM 2,45
649: DV4 SRC 2    GET NEXT RESULT DIGIT
650: RDM
651: DAA    RANGE 0-9
652: IAC    INCREMENT
653: WRM    SAVE IN RESULT (NOTE 0 IS 10)
654: DAA    CONVERT 10 TO 0
655: SRC 14    RESET SRC
656: JNC DV3    ER TO NEXT SUE IF NO CARRY
658: CLC
659: ISZ 3,DV4    GO TO THE NEXT RESULT DIGIT
661: DV6 LDM 13    RESET PRECISION
662: WR0
663: XCH 3
664: DV9 SRC 2    GET NEXT DIGIT
665: RDM
666: DV8 SRC 3 AND PUT IN OUTPUT
667: WRM
668: INC 9    INCREMENT OUT ADR
669: ISZ 13,DV7    TEST FOR DEC PT
671: LDM 11    YES OUTPUT DEC PT
672: JUN  DV8
674: DV7 ISZ 3,DV9    INC FOR NEXT DIGIT
676: SRC 14    RESET SRC
677: JUN LD
679:
  0: =679
679:
679:/
679:/ NER    PRINTS NUMERIC FIELD AND LEADING BLANKS
679:/GIVEN:  R8-R9    RAM ADR OF DATA
679:/         R10    16 - NO. OF DIGITS IN FIELD
679:/         R11    16 - NO. PRECEEDING SPACES
679: NER SRC 8    SELECT RAM
680: RDM    GET NEXT DIGIT
681: SRC 14    RESET SRC
682: XCH 3    SET DIGIT CHAR IN R2-R3
683: LDM 0
684: XCH 2
685: JMS PTC    GO PRINT CHAR
687: INC 9    INC DIGIT ADR
688: ISZ 10,NER    LOOP UNTIL ALL DIGITS PRINTED
690: NBB FIM 2,0    SET BLANK CHAR
692: JMS PTC    GO PRINT LEADING BLANK
694: ISZ 11,NBB    LOOP UNTIL ALL DIGITS PRINTED
696: BBL 12    RETURN
697:/
697:/ KEYBOARD READ - JMS SWS
697:/ RETURNS KEY NO. IN R4
697:/    CARRY OFF - DIGIT
697:/          ON  - FUNCTION
697: SWE FIM 2,61
699: JMS ADD
```

```
701: ISZ 4,SWC
703:SWS FIM 4,1    ENTRY, INITIALIZE SCAN
705: JMS LDC
707:SWC JMS DOUT   OUTPUT NEXT KEY TEST
709:SWD RDR    SENSE KEY
710: JAZ SWE   JUMP ON NO KEY
712: ISZ 15,SWD DEBOUNCE
714: ISZ 2,SWD
716: RAR   SET CARRY IF FUNCTION KEY
717:SWE RDR    WAIT FOR KEY RELEASED
718: JNZ SWE
720: ISZ 15,SWE
722: INC 4
723: BBL 0   RETURN
724:/
724:/  KYC   SENSE EOT KEY AND TURN ON TIMER
724:KYC FIM 2,13   SET RAM ADR, LOOP COUNT
726: LDM 0
727: WMP   START TIMER
728:KLP SRC 2   OUTPUT RAM PORT
729: WRR
730: INC 2   INCREMENT TO NEXT
731: ISZ 3,KLP
733: LDM 4   CHANGE LAST TO EOT BIT
734: WRR
735: SRC 14   RESTORE SRC
736: RDR   READ KEYBOARD
737: RAR
738: BBL 0   RETURN
739:/
739:
739:/  LINE   LINE FEED AND INCR LINE COUNT
739:LINE FIM 3,0
741:   SRC 3
742:   RD1
743:   IAC
744:   WR1
745: XCH 9
746: RD2
747: ADD 8
748: RAR
749: TCC
750: WR2
751: XCH 8
752: JUN PTE
754:/  READ KEYBOARD NUMBER FIELD
754:RKY JMS SWS   READ NEXT DIGIT
756:   JOC RKT    RETURN IF NOT
758:   SRC 3    SAVE DIGIT
759:   LD 4
760:   WRM
761:   LD 9    UP POINTER
762:   DAC
763:   XCH 9
764:   JOC RKY   LOOP UNTIL DONE
766:RKT BBL 2
767:
   0: =768
768:
768:/   PARM TABLE
768:/   BYTE 0   0 IF END
768:/   BIT 0-3   NO.OF DEC PLACES
768:/       4-5  00  MEAS
768:/            01  MEAS/CONSTANT
768:/            10  MEAS/MEAS
768:/            11  MEAS/MEAS/CONSTANT
768:/       6-7  00  END OF REPORT
768:/            01  PRED CONSTANT,NO 2
768:/            10  NO PRED
768:/            11  PRED FORMULA
768:/ DIVISOR MEAS ADR BYTE IF BIT 4 ON.
768:/ MEAS ADR BYTE
768:/ DIVISOR CONSTANT BYTE IF BIT 5 ON
768:/ PRED CONSTANT BYTE IF BITS 6-7 ARE 01
768:/ 8 BYTE FORMULA IF BITS 6-7 ARE 11
```

```
768:/    (AA'BB'CC'DD') WHERE 'FEMALE
768:/    PRED IS (B OR C*HT-A*AGE)/16+D+D
768:/        WHERE B CM, C INCHES, D NEG. IF ODD
768:     0
769:     0-1
770:     0+MV-1
771:     0+MVV-1
772:     0-1
773:     0+FRC-1
774:     0+FEV-1
775:     0-1
776:     0-1
777:     0-1
778:FEV  224+3    FEV
779:     29
780:     35
781:     29
782:     35
783:     66
784:     216
785:     167
786:     187
787:     135
788:     91
789:     224+3    FEV.5
790:     214
791:     34
792:     18
793:     33
794:     29
795:     85
796:     72
797:     12
798:     15
799:     162
800:     224+3    FEV1
801:     223
802:     44
803:     34
804:     60
805:     45
806:     152
807:     114
808:     85
809:     43
810:     164
811:     224+2    FEV2
812:     232
813:     165
814:     224+2    FEV3
815:     241
816:     166
817:     0+9      TVC1
818:     29
819:     223
820:     83
821:     174
822:     0+9      TVC2
823:     29
824:     232
825:     94
826:     175
827:     0+9      TVC3
828:     29
829:     241
830:     97
831:     176
832:     0+7      PEFR
833: 208
834: 27
835: 25
836: 27
837: 3
838: 0
839: 8
```

```
840: 0
841: 254
842: 202
843:    170
844:    0+11    FEF0-25   5
845:    26
846:    23
847:    45
848: 35
849: 41
850: 55
851: 105
852: 139
853: 60
854: 75
855:    130
856:    224+15   FEF25-75
857:    20
858:    17
859:    60
860:    72
861:    43
862:    30
863:    38
864:    75
865:    96
866:    126
867:    28
868:    187
869:    0
870:MVV 0+15    MVV
871:    20
872:    23
873:    200
874:    20
875:    10
876:    21   21
877:    13
878:    54
879:    33
880:    11
881:    3
882:    113
883:    0+13    MVR
884:    20
885:    26
886:    200
887:    90
888:    114
889:    240+5   MVT
890:    20
891:    208
892:    100   10
893:    112
894:    0
895:MV  0+14    MV
896:    20
897:    23
898:    200
899:    115
900:    224+10   TV
901:    26
902:    23
903:    178
904:    0+14    RR
905:    20
906:    26
907:    200
908:    122
909:    0
910:FRC  224+3   FRC
911:    37
912:    0
913:    0
914:    54
915:    43
916:    130
```

```
917: 104
918: 147
919: 117
920: 124
921: 224+2    IC
922: 17
923: 127
924: 224+2   ERV
925: 20
926: 130
927: 224+3
928: 23      RV
929: 256-19
930: 256-15
931: 32
932: 26
933: 80
934: 64
935: 113
936: 91
937: 121
938: 224+3
939: 26      TLC
940: 0
941: 0
942: 100
943: 80
944: 255
945: 204
946: 235
947: 187
948: 133
949: 0+11    RV/TLC
950: 26
951: 23
952: 256-3
953: 256-3
954: 0
955: 0
956: 0
957: 0
958: 18
959: 18
960: 117
961: 0
962:
  0: =976
976:

976:

976:

976:LMS FIM    2      GET NEXT VALUE
977:    JMS    IPT
979:    JUN    LD
981:GPRM FIM   4      GET NEXT FACTOR,MALE OR FEMALE
982:    JMS    IPT
984:    FIM    6,52
986:    SRC    6
987:    RDM
988:    SRC    14
989:    DAC
990:    JAZ    *+3    SKIP IF MALE
992:LMT FIM    4      GET CONSTANT ENTRY
993:    LD     5
994:    XCH    12
995:    FIM    2,40   STORE FACTOR
997:    JMS    STC
999:LMC FIM    4      ANOTHER CONSTANT ENTRY
1000:IPT ISZ   1,*+3  UPDATE PARM PTR ROUTINE
1002:   INC    0
1003:   BBL    3
1004:HDD 215
1005:RPP FIM   12     ENTRY,GET PARM ENTRY ATR.
```

```
1006:     FIM   0,HDD  SET UP HEADING PRINT
1008:RLP  FIN   8      GET TEXT ADR
1009:     JMS   PTT+2  AND PRINT IT
1011:     LD    12     RESTORE PARMPTR.
1012:     XCH   0
1013:     LD    13
1014:     XCH   1
1015:     FIM   2,0    CLEAR OUTPUT AREA
1017:     JMS   CLR
1019:     JMS   IPT    UPDATE PARM PTR.
1021:     FIN   10     GET CONTROL BYTE
1022:     JMS   IPT
1024:/ END OF ROM
1024:
  0: =1024
1024:
1024:     JMS   LMS    GET MEAS
1026:     LD    11
1027:     JAZ   CPL    TERMINATE IF LIST END
1029:     RAL
1030:     JNC   NDVM   JUMP NOT MEAS DIVIDE
1032:     FIM   2,40   SAVE DEVISOR
1034:     JMS   STO
1036:     JMS   LMS    GET DIVIDEND
1038:     FIM   3,4    DUMMY BCD
1040:     JMS   DIV
1042:NDVM FIM   4,100  SET UP 100 DIVISOR
1044:     FIM   2,40
1046:     LD    11
1047:     RAL
1048:     RAL
1049:     JNC   *+4    JUMP NOT CONSTANT DIVISOR
1051:     JMS   IPT-1  GET CONSTANT
1053:     JMS   STC    STORE DIVISOR
1055:     FIM   8,4    OUTPUT MEAS
1057:     JMS   DTT+2  WITH BINARY IN 32
1059:     XCH   11
1060:     RAR
1061:     JNC   PPD+10 JUMP NO PREDICTION
1063:     RAR
1064:     JOC   *+6    JUMP PRED FORMULA
1066:     JMS   IPT-3  GET PRED CONSTANT
1068:     JUN   PPD
1070:     LDM   12     SET 16 BIT PRECISION
1071:     WR0
1072:     FIM   8,57   AGE
1074:     LDM   14
1075:     JUN   EPTCH
1077: JMS STO
1079:     JMS   INCM
1081:     JUN   APTCH  MM
1083:     JMS   SUB
1085:     LDM   13     DIVIDE BY 16
1086:     WR0
1087:     JMS   GPRM   SUBTRACT 2X THIRD TERM
1089:     LD    12
1090:     RAR
1091:     LDM   3
1092:     DAA
1093:     RAL
1094:     JMS   SET
1096:     JMS   SET+3
1098:     JMS   STO    SAVE PRED
1100:     XCH   3
1101:     JMS   LD     GET MEAS
1103:     FIM   8,0    OUTPUT PCT
1105:     JMS   DIV
1107:     FIM   4,75   80 COMPARE WITH 80 %
1109:     JMS   STC
1111:     JMS   SUB
1113:     LDM   12     SET BLANK OR HYPHEN
1114:     JNC   PPD
1116:     XCH   11     AND SAVE
1117:PPD  FIM   4,100  OUTPUT PRED
1119:     JMS   LDC
```

```
1121:   FIM 2,40
1123:   JMS XCH
1125:   JMS DTT
1127:     LD 0    SAVE PARM PTR
1128:     XCH 12
1129:     LD 1
1130:     XCH 13
1131:     JMS PTS   START PRINTER
1133:     LD 11     GET AE/DCMAL INDICATOR
1134:     FIM 3,15
1136:     FIM 10,207
1138:     JMS NER+3  PRINT PCT
1140:     INC 9
1141:     FIM 10,207
1143:     JMS NER     PRINT MEAS
1145:     FIM 10,206
1147:     JMS NER      PRINT PRED
1149:     LD 12        RESTORE PARM PTR
1150:     XCH 0
1151:     LD 13
1152:     XCH 1
1153:     JUN IPT+3        GO PRINT MEAS TEXT
1155:MMM XCH 13         SAVE DIGIT COUNT
1156:     JMS GPEM     GET NEXT FACTOR
1158:     JMS CLA      CLEAR ACC
1160:     FIM 2,44   MULT EY 10
1162:     LDM 7
1163:     JMS MLT
1165:     FIM 2,40      MULT FACTOR BY NEXT DIGIT
1167:     SRC 5
1168:     RDM
1169:     DAA
1170:     JAZ *+9
1172:     DAC
1173:     XCH 5
1174:     JMS ADD
1176:     LD 5
1177:     JNZ *-5
1179:     LD 9
1180:     DAC
1181:     XCH 9
1182:     ISZ 13,MMM+5 LOOP ON ALL DIGITS
1184:     FIM 2,12
1186:     BBL 0
1187:DTT FIM 3,8
1189:     LD 10
1190:     JIN DIV
1192:INCM FIM 2,55   ENTER WITH CARRY OFF
1194:     SRC 2      TEST INCHES/CM
1195:     LDM 13
1196:     ADM
1197:     JNC *+8      JUMP ON CM
1199:     FIM 2,53   SET INCH FLAG
1201:     SRC 2
1202:     LDM 12
1203:     WRM
1204:     BBL 14    RETURN TWO DIGIT ENT
1205:     BBL 13    RETURN 3 DIGIT ENT
1206:PRINT JMS DCL   START PRINTER
1208: WMP
1209:     JMS LINE  LINE FEED
1211: NOP
1212: NOP
1213: NOP
1214: NOP
1215: NOP
1216: NOP
1217: NOP
1218: NOP    DM 6   TEST FOR
1219:PID FIM 3,198     PRINT ID HEADING
1221: JMS PTT
1223: JMS PTS     PRINT ID DATA
1225: FIM 8,48
1227: FIM 10,206   CE    REF NO.
1229: JMS NER
```

```
1231: SRC 8     SEX
1232: ADM
1233: FIM 10,254    FE
1235: JMS NER+2
1237: JMS INCM
1239: FIM 10,222   HEIGHT
1241: JMS NER
1243: FIM 10,239   AGE
1245: JMS NER
1247: JMS LINE    LINE/RETURN
1249: SRC 0
1250: RD0
1251: SRC 14
1252: XCH 4
1253: LDM 7
1254: ADD 4   1
1255: JAZ JEE    GO TO JOE IF ID
1257: JMS LINE
1259: LD 4
1260: XCH 1   D
1261: JUN IPT+5
1263: CPL  JMS LINE   SKIP TO BOTTOM
1265: JMS LINE
1267: FIM 8,94    TEAR OFF
1269: JMS PTT
1271: JMS LINE
1273: JMS LINE
1275: JEB JUN JOE   GO TO JOE CONTROL
1277: ?
    0: =1280
1280:
1280: ANA FIM  10,0    ***** START ANALOG ENTRY
1282:     FIM   2,58   CLEAR SEARCH INCR, DIGITAL VALUE
1284:     JMS   CLR
1286:     JMS   ALP    SEEK CURRENT ANALOG VALUE
1288:     JMS   ALP
1290: RSA FIM   2,16   ***** RESET ANALOG ENTRY
1292: RSB JMS   CLR    CLEAR REGISTER
1294:     FIM   2,14   INITIALIZE MINIMUM (13)
1296:     FIM   4,127
1298:     JUN   STC    AND RETURN
1300: NXA JMS   STO    STORE WHATEVER
1302:     JMS   KYC    ***** NEXT ANALOG ENTRY
1304:     JOC   EE     BRANCH IF EOT KEY
1306:     FIM   2,45   GET LAST ADC VALUE
1308:     JMS   LD
1310: ALP JMS   DOUT   OUT NEXT TO DAC
1312:     LDM   3      SET HIGH/LOW
1313:     JCN   1,*+5
1315:     JMS   STO-4     TIMING PAD
1317:     LDM   6
1318:     XCH   7      SEVE AND GET PREV
1319:     SUB   7      COMPARE AND SET CARRY EOR
1320:     RAR
1321:     RAR
1322:     FIM   2,58   GET INCREMENT
1324:     SRC   2
1325:     RDM
1326:     JNC   *+3
1328:     LDM   0      RESET IF DIRECTION CHANGE
1329:     RAL          MULTIPLY BY 2
1330:     JNZ   *+3
1332:     LDM   12     LIMIT TO 12
1333:     WRM
1334:     JMS   SET+1  GO ADD OR SUBTRACT
1336:     FIM   12,6   UPDATE FOR 126 CYCLES FS
1338:     JMS   UPTH
1340:     JNC   ALP    JUMP NOT COMPLETE
1342:     FIM   2,45   SAVE ANALOG VALUE
1344:     JMS   STO
1346:     XCH   2      COMPARE TO MINIMUM
1347:     JMS   SUB
1349:     FIM   12,15+34
1351:     JNC   NNMN   BRANCH NOT NEW MIN
1353:     JMS   ADD    SAVE NEW MINIMUM
```

```
1355:      JMS  STO
1357:
1357:NGT   BBL  1
1358:NMMN  XCH  3       TEST 100CC THRESHOHD
1359:      FIM  4,10
1361:      SRC  2       TEST IF FEV
1362:      RD0
1363:      SRC  14
1364:      ADD  5
1365:      JNZ  *+3
1367:      INC  4
1368:      JMS  STC
1370:      INC  13
1371:      JMS  SUE
1373:      JOC  NGT     RETURN IF NOT ABOVE
1375:      JUN  ADD     RESTORE VALUE AND RETURN
1377:      NOP  URN
1378:/ RETURN 0 NC  ADC-MIN
1378:/          0 C   EOT KEY
1378:/          1 NC  NEW MIN
1378:/          1 C   NOT ABOVE THRESHOLD
1378:UPTM  CLC          ***** INCR TIMER BY R12-13
1379:      LD   13       BY 1 FOR EACH 21 CYCLES 3
1380:      ADD  11
1381:      XCH  11
1382:      LD   12
1383:      ADD  10
1384:      XCH  10
1385:EE    BBL  0        RETURN
1386:PUSH  FIM  6,195 ***** PUSH DOWN STACK
1388:      FIM  2,198
1390:LPS   SRC  6       MOVE NEXT VALUE
1391:      RDM
1392:      SRC  2
1393:      WRM
1394:      ISZ  3,*+3   INCREMENT ADDRESSES
1396:      INC  2
1397:      ISZ  7,LPS   AND LOOP UNTIL DONE
1399:      ISZ  6,LPS
1401:      SRC  14
1402:      JUN  STO     PUT IN NEW VALUE AND RETURN
1404:MPY   FIM  2,58    MULTIPLY WITH FIXED WORK AREA
1406:MLT   XCH  5
1407:      JMS  STO     SAVE ACC
1409:      JMS  ADD
1411:      ISZ  5,*-2   LOOP UNTIL DONE
1413:      BBL  0       RETURN
1414:PTT   JMS  DCL     STAR PRINTER
1416:      WMP
1417:      JMS  PTS     STAR PRINT LINE
1419:      CLC
1420:      JUN  PTX     PRINT TEXT
    0:  =1422
1422:
1422:MVV   JMS  AMA  ***** MVV MEANS ROUTINE
1424:      JMS  MNMX    START ADC AND FIND INITIAL MIN/MAX
1426:      JOC  ABT     BRANCH IF TEST ABORT
1428:      JMS  RSA     RESET TIME
1430:      XCH  9
1431:VLP   FIM  2,17    SAVE LAST PEAK TIME
1433:      JMS  LD
1435:      FIM  2,20
1437:      JMS  STO
1439:      FIM  12,116  UPDATE TIME USED
1441:      JMS  MNMX    GET NEXT MIN/MAX PAIR
1443:      JOC  E       BRANCH END OF TEST
1445:      FIM  2,23    INCREMENT TOTAL VOLUME
1447:      JMS  ADD
1449:      JNC  NOVR    BR NOT >20,47 LITER
1451:      RDM          RESET SIGN BIT
1452:      RAL
1453:      CLC
1454:      RAR
1455:      WRM
1456:      INC  9       INCREMENT OVERFLOW COUNT
```

```
1457:NOVR JMS STO       SAVE
1459:     FIM 4,25      INCREMENT COUNT BY 25
1461:     JMS LDC
1463:     FIM 2,26
1465:     JMS ADD
1467:     JMS STO
1469:     JUN VLP   GO UPDATE TIME
1471:E    FIM 2,23 DEVIDE VOLUME BY 4
1473:     LDM 12
1474:     WR0
1475:     JMS LD
1477:     FIM 2,60
1479:     JMS ADD
1481:     LD 9
1482:     WRM
1483:     JMS ADD
1485:     LDM 13
1486:     WR0
1487:     FIM 2,23      SAVE IT
1489:     JMS STO
1491:     JUN JOB       GO TO JOB
1493:ABT  JUN ABORT
1495:MNMX FIM 2,10   ***** MIN/MAX PAIR ROUTINE
1497:     JMS RSE   INITIALIZE
1499:SMN  FIM 4,1   UPDATE RUNNING TIME
1501:     JMS LDC
1503:     JMS UPTM
1505:     FIM 2,17
1507:     JMS ADD
1509:     JMS NXA       GET NEXT ANALOG
1511:     FIM 12,74
1513:     JNZ SMN       LOOP NEW MIN OR < 100 CC
1515:     JOC EE
1517:     FIM 2,10      COMPARE WITH MAX
1519:     JMS SUB
1521:     JNC MXX       JUMP ON NEW MAX
1523:     XCH 3         TEST 100 CC THRESHOLD
1524:MXX  JMS ADD
1526:     FIM 12,34  19
1528:     JMS STO
1530:     JNC SMN       JUMP NOT DONE
1532:     FIM 2,10      GET MAX-MIN VOLUME
1534:     JUN LD        AND RETURN
1536:/ 17 RUNNING TIME
1536:/ 20 LAST PEAK TIME
1536:/ 23 TOTAL VOLUME/4
1536:/ 26 CYCLE COUNT X 25
1536:
   0: =1536
1536:
1536:FV  JMS ANA    STAR AI
1538:    FIM 8,6    SET .2 SEC
1540:IPT FIM 10,165   SET APPROX 40 SAMPLES PER SECOND
1542:    ISZ 9,BAI  UPDATE .2 SEC TIMER
1544:    FIM 8,15   FREEZE AT TIME END, AND RESET SAMPLING
1546:BAI JMS NXA+2   GET NEXT MEAS
1548:    JNZ IPT    JUMP TEST NOT STARTED
1550:    JOC JBB    JUMP ON CANCEL TEST
1552:    FIM 2,23   POINT TO PEAK FLOW
1554:    LD 3
1555:    JNZ NFR    JUMP NOT FIRST MEAS
1557:    JMS STO SAVE TEMPORARILY
1559:    ISZ 9,JBB   ABORT IF BAD START
1561:    FIM 10,49
1563:    JUN UTM+2
1565:NFR SUB 14     TEST FOR 1/6 SEC
1566:    FIM 12,46
1568:    JNC UTM    JUMP NOT YET
1570:    JNZ NSC    JUMP PAST 1/6 SEC
1572:    FIM 10,69
1574:    JMS SUB    COMPUTE RATE
1576:    JMS XCH    AND SAVE
1578:NLP FIM 12,4    EXTRAPOLATE TO ZERO
1580:    JMS UPTM
1582:    JMS SUB
```

```
1584: JOC NDN   JUMP PAST QERO
1586: LDM 3    INCREMENT COUNTER BY 3
1587: ADD 8
1588: XCH 8
1589: JNC NLP   JUMP NOT PAST 1 SEC
1591: JUN JEE
1593:ZUP JMS UPTM
1595: JNC *+3
1597: FIM 12,23
1599: JMS UPTM
1601: INC 8
1602: STC
1603: BBL 13
1604: NOP
1605: NOP
1606:JEE LDM 1      ABORT
1607: JUN IDS+1
1609:NDN JMS ADD   INTERPOLATE TO 10 MS RESOLUTION
1611: LDM 12   MULTIPLY REMAINDER BY 16
1612: WR0
1613:ELP FIM 12,49   INCREMENT TIME BY 1/96 SEC
1615: JMS ZUP
1617: JMS SUB   SUBTRACT RATE
1619: JNC ELP   LOOP UNTIL PAST ZERO
1621: FIM 14,60   RESTORE ADC INCREMENT
1623: SRC 14
1624: WRM
1625: LDM 13   RESTORE PRECISION
1626: WR0
1627: LD 8   SAVE COUNTER
1628: XCH 4
1629: JMS CLA   CLEAR ACC
1631:SLP JMS PUSH   PUT NEXT VALUE IN STACK
1633: FIM 2,23
1635: JMS ADD   ADD RATE
1637: FIM 12,30   UP TIME
1639: JMS ZUP
1641: ADD 4   SUBTRACT 3 FROM COUNT
1642: XCH 4
1643: JOC SLP   LOOP UNTIL NEGATIVE
1645: FIM 2,13   SET NEXT 1/6 SEC VALUE FOR ADC
1647: JMS ADD
1649: FIM 2,45
1651: JMS STO
1652: JUN UTM+2      13
1655:NSC FIM 12,47 ,    TEST SAMPLE 6,9,12,15
1657: IAC
1658: ADD 14
1659: JNC *-1
1661: JNZ UTM   JUMP NO
1663: JMS PUSH   ADD TO STACK
1665: FIM 12,73   2,
1667:UTM JMS UPTM   UPDATE TIME
1669: ISZ 8,EAI   LOOP FOR 5/6 SEC
1671: FIM 8,93    5D   SET SAMPLE/SAVE COUNTERS
1673:EE FIM 0,256-20    TIMEOUT COUNTER (2 SEC)
1675:E JMS NXA+2   GAI
1677: FIM 12,56   UPDATE TIME   M
1679: LD 9
1680: JAZ F   JUMP END OF SAMPLED DATA
1682: ISZ 9,F   JUMP NOT SAMPLE TO SAVE
1684: FIM 12,33   UPDATE TIME   TM
1686: JMS PUSH
1688: LDM 10
1689: ISZ 8,*+3   UP SAMPLE COUNTER, IF NOT END,
1691: LDM 0
1692: XCH 9   5   RESET SAVE COUNTTER
1693:F FIM 2,29   COMPARE WITH MAX
1695: JMS UPTM   X
1697: JMS SUB
1699: JOC G JUMP NOT NEW MAX
1701: JMS ADD SAVE NEW MAX
1703: JMS STO
1705: JUN EE   GO RESET TIMEOUT
1707:G JMS LD
```

```
1709:   FIM 2,253
1711:   JMS STO
1713:   ISZ 1,E   DECREMENT TIMEOUT
1715:   ISZ 0,E   END IF TIMED OUT
1717:   LD 3
1718:   JAZ DNN
1720:   JMS PUSH
1722:   ISZ 3,*-2
1724:DNN JUN MMEF
1726:
   0: =0
   0:
   0: =1751  8
1751:APTCH XCH 13
1752:   JMS  GPRM
1754:   LDM  2
1755:   ADD  13
1756:   JOC  INCH
1758:   JMS IPT
1760:   JMS IPT
1762:RT  JMS  MMM+3
1764:   JUN 1083
1766:INCH JMS  GPRM
1768:   JUN  RT
1770:EPTCH XCH 13
1771:   JMS GPRM
1773:   FIM 2,41
1775:   SRC 2
1776:   RDM
1777:   RAL
1778:   JNC RTE
1780:   INC 3
1781:   SRC 2
1782:   LDM 15
1783:   WRM
1784:   INC 3
1785:   SRC 2
1786:   WRM
1787:RTE SRC 14
1788:   JMS MMM+3
1790:   JUN 1077   5
1792:GPRM =981
1792:IPT =1000
1792:MMM =1155
1792:
   0: =1792
1792:
1792:MMEF LDM 12   COMPUTE 1/4 FEV
1793:   WR0
1794:   FIM 2,29
1796:   JMS LD
1798:   WRM
1799:   FIM 2,60
1801:   JMS ADD
1803:   JMS ADD
1805:   LDM 13
1806:   WR0
1807:   FIM 2,13
1809:   FIM 4,2
1811:   JMS STC
1813:   FIM 2,23   SAVE 1/4 FEV
1815:   JMS STO
1817:   FIM 4,0
1819:   JMS SUB
1821:   JMS SUB
1823:   FIM 2,10
1825:   JMS STO  R
1827:   XCH 12   ZERO STACK COUNT
1828:   JMS SRC   SEARCH FIRST 1/4 FEV
1830:   FIM 2,26  SAVE IT
1832:   JMS STO
1834:   FIM 2,29  COMPUTE 3/4 FEV
1836:   JMS LD
1838:   FIM 2,23
1840:   JMS SUB
```

```
1842: JMS STO     SAVE IT
1844: JMS ADD  COMPUTE 3X1/2 FEV
1846: FIM 2,17
1848: JMS STO    SAVE IT
1850: FIM 2,253
1852: JMS LD
1854: JMS SCT    FG CONT FOR 3/4 FEV
1856: FIM 2,26  COMPUTE SXTIME
1858: JMS SUE
1860: FIM 2,20
1862: JMS STO   SAVE IT
1864: INC 12    RESTORE STACK
1865:CLP JMS NEXT
1867: ISZ 12,CLP
1869: JUN FEN    DONE
1871:NEXT FIM 2,203   GET NEXT ENTRY
1873: JMS LD
1875: JUN PUSH
1877:SRC JMS NEXT   GET NEXT
1879:SCT FIM 2,23  COMPARE
1881: JMS  SUE
1883: JNC ESCN   GO TO SUBSCAN
1885: FIM 2,10 0
1887: JMS STO
1889: LDM 9
1890: ADD 12
1891: TCC
1892: IAC
1893: XCH 4
1894: INC 5  0
1895: JMS LDC    INCREMENT TIME
1897: FIM 2,13
1899: JMS ADD
1901: JMS STO
1903:SLP ISZ 12,SRC   C
1905: JUN TLM   TIME LIMIT
1907:ESCN FIM 2,10   VOLUME DIFFERENCE
1909: JMS SUE
1911: LDM 12   CONVERT ACC TO 16 BIT  16
1912: WR0
1913: FIM 2,61
1915: JMS LD
1917: WR1
1918:  FIM 2,9    MULT REMAINDER BY 16  0
1920: JMS XCH   AND SAVE
1922:SRL JMS ADD    ADD INCR
1924: JNC FFD   LOOP UNTIL INTERSECT
1926: ISZ 5,SRL
1928: INC 4
1929:FFD LDM 13
1930: WR0
1931: JMS LDC   AND LOAD IT
1933: LDM 10    11
1934: ADD 12
1935: JNC NEL   E
1937: FIM 2,61
1939: JMS ADD
1941:NEL FIM 2,13   ADD TO TIME
1943: JMS ADD
1945:TLM LDM 12   MULTIPLY BY 5
1946: JUN MPY    AND RETURN
1948:
   0: -
   0: =2109
2109:
2109:FRC JMS KYC    START TIMER
2111: FIM 10,13   DIGIT COUNT
2113: FIM 2,37   CLEAR FRC
2115: JMS CLR
2117:LPA JMS SWS   READ DIGIT
2119: JNC DIG   JUMP ON DIGIT
2121:ABT JUN ABORT   GO ABORT TEST
2123:DIG FIM 2,37   GET FRC SO FAR
2125: JMS LD
2127: LDM 7    MULTIPLY BY 10
```

```
2128: JMS MLT
2130: XCH 4     ADD NEW DIGIT
2131: DAA
2132: XCH 5
2133: JMS STC
2135: JMS ADD
2137: JMS STO    SAVE FRC
2139: ISZ 11,LPA   GO TO NEXT DIGIT FOR 3 DIGITS
2141: FIM 8,124   PRINT FRC
2143: JMS DCL
2145: LDM 2
2146: WMP
2147: JMS PTT+3
2149: LDM 0
2150: WMP   P
2151: FIM 2,256-16   CLEAR STACK
2153: JMS CLR
2155: JMS ANA    START ANALOG, CLEAR MAX(17)
2157: JMS MNMX   GET FIRST MIN/-MAX
2159: JOC AET
2161: FIM 2,21    INITIALIZE MIN. (20)
2163: FIM 4,127
2165: JMS STC
2167:LPE JMS MNMX   GET NEXT MIN-MAX
2169: JOC TED    TEST END
2171: FIM 2,13    ADD LOCAL MIN
2173: JMS ADD
2175: JMS PUSH    PUT IN STACK
2177: FIM 2,29    TEST PEAK
2179: JMS SUB
2181: JOC NMX    JUMP NOT NEW PEAK
2183: JMS ADD
2185: JMS STO
2187: XCH 9    SET LAST PEAK IND
2188: FIM 2,256-6    COMPUTE AVH MV
2190: JMS LD
2192: FIM 2,256-9
2194: JMS ADD
2196: FIM 2,23    SAVE
2198: JMS STO
2200: JUN LPE
2202:NMX FIM 2,13   GET LOCAL MIN
2204: JMS LD
2206: FIM 2,20    TEST NEW MIN
2208: JMS SUB
2210: JNC LPE    JUMP NOT NEW MIN
2212: JMS ADD SAVE IT
2214: JMS STO
2216: FIM 8,1    SET LAST MIN IND
2218: FIM 2,256-9    COMPUTE AVH MV
2220: JMS LD
2222: FIM 2,256-12
2224: JMS ADD
2226: FIM 2,26    AND SAVE IT
2228: JMS STO
2230: JUN LPE
2232:TED FIM 2,23   GET MV
2234: LD 9
2235: JNZ E
2237: FIM 2,26
2239:B LDM 12
2240: JMS DV2N    DIVIDE BY 2
2242: FIM 2,20    SUBTRACT MIN
2244: JMS SUB
2246: FIM 2,17    SAVE IC
2248: JMS STO
2250: FIM 2,37    ADD FRC
2252: JMS ADD
2254: FIM 2,26    SAVE TLC
2256: JMS STO
2258: FIM 2,29
2260: JMS SUB    SUBTRACT PEAK
2262: FIM 2,20
2264: JMS ADD
2266: FIM 2,23    SAVE RV
```

```
2268: JMS STO
2270: FIM 2,37
2272: JMS LD
2274: FIM 2,23    S XCH
2276: JMS SUB
2278: FIM 2,20    SAVE ERV
2280: JMS STO
2282: JUN JOB
2284: DV2N XCH 5   DIVIDE BY 2N (2,4,8, OR 16)
2285: LDM 12    ACC - DIVIDE BY
2286: WR0         15      16
2287: JMS LD      14      8
2289: WRM         13      4
2290: FIM 2,60    12      2
2292: JUN DVB    REMAINDER IN RAM 60
2294: DVA JMS ADD
2296: DVB ISZ 5,DVA
2298: LDM 13
2299: WR0
2300: BBL 0
2301: ?
        =2043
2048: FBC FIM 2,256-16    CLEAR STACK
2050: JMS CLR
2052: JMS ANA    START ANALOG, CLEAR MAX(17)
2054: JMS MNMX   GET FIRST MIN/MAX
2056: JOC ABT
2058: FIM 2,21    INITIALIZE MIN. (20)
2060: FIM 4,127
2062: JMS STC
2064: LPB JMS UNMX   GET NEXT MIN-MAX
2066: JOC TED    TEST END
2068: FIM 2,13    ADD LOCAL MIN
2070: JMS ADD
2072: JMS PUSH    PUT IN STACK
2074: FIM 2,29    TEST PEAK
2076: JMS SUB
2078: JOC NMX    JUMP NOT NEW PEAK
2080: JMS ADD
2082: JMS STO
2084: XCH 9    SET LAST PEAK IND
2085: FIM 2,256-6    COMPUTE AVH MX
2087: JMS LD
2089: FIM 2,256-9
2091: JMS ADD
2092: FIM 2,22    SAVE
2095: JMS STO
2097: NMX FIM 2,13    SET LOCAL MIN
2099: JMS LD
2101: FIM 2,20    TEST NEW MIN
2103: JMS SUB
2105: JNC LPB    JUMP NOT NEW MIN
2107: JMS ADD    SAVE IT
2109: JMS STO
2111: FIM 3,1    SET LAST MIN IND
2113: FIM 2,256-9    COMPUTE AVH MN
2115: JMS LD
2117: FIM 2,256-12
2119: JMS ADD
2121: FIM 2,26    AND SAVE IT
2123: JMS STO
2125: JUN LPB
2127: TED FIM 2,23    GET MV
2129: LD 9
2130: JNZ B
2132: FIM 2,26
2134: B JMS LGL
2136: FIM 4,77
2138: JMS STC
2140: JMS SUB
2142: JMS ALOG
2144: FIM 2,20    SUBTRACT MIN
2146: JMS SUB
2148: FIM 2,17    SAVE IC
2150: JMS STO
```

```
2152: FIM 0,256-70   4 SECOND DELAY
2154:LPD JMS ALP  +2
2156: ISZ 1,LPD
2158: ISZ 0,LPD
2160: FIM 0,256-4*1   SET TO READ 3 CHANNELS
2162: SRC 0
2163:LTI LD 1      4TH INPUT CHANNEL
2164: WMP
2165: SRC 14
2166: FIM 2,33
2168: JMS CLP
2170: JMS ALP
2172: JMS ALP-1
2174: JMS ALP-1
2175: FIM 3,45
2178: JMS LD
2180: JMS PUSH   ADD TO STACK
2182: INC 1    UPDATE TO NEXT
2183: SRC 2
2184: ISZ 0,LTI   LOOP ON 3 CHANNELS
2186: WMP    RESTORE CHANNEL 0
2187: SRC 14
2188: FIM 2,256-9   NE
2190: JMS LGL
2192: JMS STO
2194: FIM 2,29
2196: JMS LD
2198: FIM 2,20
2200: JMS SUB
2202: JMS STO   VC
2204: JMS LOG
2206: LDM 2
2207: ADM
2208: WRM
2209: JMS SUB
2211: JMS ALOG
2213: FIM 2,26
2215: JMS STO TLC
2217: FIM 2,20
2219: JMS SUB
2221: FIM 2,23
2223: JMS STO   BW
2225: FIM 2,26
2227: JMS LD
2229: FIM 2,17
2231: JMS SUB
2233: FIM 2,27
2235: JMS STO   FRC
2237: FIM 2,256-5  CO
2239: JMS LGL
2241: FIM 4,134
2243: JMS STC
2245: JMS ADD
2247: JMS STO
2249: FIM 2,256-9   NE
2251: JMS LGL
2253: JMS SUB
2255: JMS LOG
2257: FIM 4,137
2259: JMS STC
2261: JMS ADD
2263: JMS STO
2265: FIM 2,256-3   P
2267: JMS LGL
2269: JMS SUB
2271: JMS STO
2273: FIM 2,20   VC
2275: JMS LGL
2277: JMS SUB
2279: JMS ALOG
2281: FIM 2,20    DLCO
2283: JMS STO
2285: JMP JOE
2287:ABT JMP ABORT
2289:<<<>>>??
```

```
       =2204
2204:/  12 BIT PRECISION ONLY ROUTINES
2204:/  LOG     A=LOG10(A)*256
2204:/  ALOG    A=10**A/256
2204:/  USES 16 BIT ACCUMULATOR, ALL OF RAM REG 0, AND R1-R7,R15,R14
2304:/  LTB ADR MUST BE A MULTIPLE OF 16
2304:LTB 103    SECOND SUBTRACT CONSTANT
2305:    7       THIRD
2306:   FIM 0,12+LTB
2308:   LDM 6   6
2309:CON XCH 3   SET RAM ADR
2310:   FIM 4    GET CONSTANT
2311:   INC 1    INCREMENT FOR NEXT
2312:   LDI 12   SET 12 BIT PRECISION
2313:   WR0
2314:   JUN STC  GO STORE CONSTANT
2316:   59       LOG INITIAL VALUE
2317:   58
2318:   209      FIRST SUBTRACT CONSTANT
2319:   4
2320:LGL JMS LD  LOG LOAD ENTRY
2322:LOG FIM 2,0 LOG ENTRY, SET S AT 0
2324:   JMS CLR  AS 00XXX0
2326:   INC 3
2327:   JMS STO
2329:   JMS CON-3
2331:   LDM 8    8
2332:   JMS CON
2334:CM  LDM 10  SET 1233 AT 10
2335:   JMS CON
2337:   LDM 12
2338:LPA JMS CON SET NEXT SUBTRACT CONSTANT
2340:LP  FIM 2,6 GET Y
2342:   JMS LD
2344:   FIM 2,10 SUBTRACT CONSTANT
2346:   JMS SUB
2348:   FIM 2,6
2350:   JCN NY   END LOOP IF UNDERFLOW
2352:   JMS STO
2354:   LD 1     MULTIPLY Y BY 2,17/16, OR 257/256
2355:   XCH 3
2356:   JMS LD
2358:   XCH 3
2359:   JMS ADD
2361:   LDI 6
2362:   JCN NX   END LOOP IF OVERFLOW
2364:   JMS STO
2366:   JUN LP   GO CONTINUE ITERATION
2368:NX  XCH 2   SAVE RESULT ADR
2369:   LDM 13   TEST FOR LAST PASS
2370:   ADD 1
2371:   LDM 10   SUBTRACT CONSTANT ADR
2372:   JIC LPA  GO LOOP IF NOT LAST PASS
2374:   FIM 3,3  HALF ROUND RESULT
2376:   JMS LDC
2378:   JMS ADD
2380:   LDM 12   RESTORE 12 BIT PRECISION
2381:   WR0
2382:   FIM 2,40
2384:   BBL 0    RETURN
2385:ALGL JMS LD ALOG LOAD ENTRY
2387:ALOG FIM 2,0 ALOG ENTRY, SETUP X AS 000010
2389:   JMS CLR
2391:   FIM 4,13
2392:   JMS CON+3
2395:   FIM 2,3
2397:   JMS STO
2399:   SRC 3
2400:   LDM 4
2401:   WRM
2402:   SRC 12
2403:   FIM 0,14+LTB
2405:   JUN CM   GO SET FIRST SUBTRACT CONSTANT
2407:
```

We claim:

1. A self-contained, portable system for measuring and computing respiratory parameters of a test subject undergoing forced expired breathing maneuvers according to instructions, comprising: transducer means including spirometer means receiving the exhaled breath of the subject for generating a measurement signal representative of the volume of gas exhaled by said subject during a predetermined forced breathing maneuver; miniaturized digital computer means including clock circuit means for generating timing signals, said computer means receiving said measurement signal for acquiring and storing digital signals representing a stored record of said forced maneuver, in timed relation with said timing signals and for computing predetermined respiratory parameters of said subject from said stored signals; keyboard means comprising a plurality of digit key means selectively actuatable by an operator and communicating with said computer means for entering data relating to said particular subject, and a plurality of function key means for controlling the acquisition of said stored record of a forced breathing maneuver from said spriometer means in timed relation with said timing signals, and for communicating with said computer means for controlling the sequence of operation and computation of said system; and record generating means including printer means for printing alpha-numeric characters on a paper tape under control of said computer means to generate indicia representative of the computed parameter results selected by the operator through said keyboard means, and for communicating to said operator the progress of the sequence of said operations of said system under control of said computer means.

2. The system of claim 1 further comprising: conducting bus means for transmitting digital signals from said computer means to said record generating means and said keyboard means; digital-to-analog conversion means responsive to the signals on said bus means representative of the volume of gas exhaled by said subject at predetermined sample times during a given breathing maneuver for converting said digital signals to a representative first analog signal; comparator circuit means responsive to said first analog signal and the output measurement signal of said spirometer means for generating an output signal representative of whether said first analog signal is greater than or less than the output signal of said spirometer means, said computer means being a programmable digital computer and responsive to the output signal of said comparator circuit means and programmed for generating successive approximations of said spirometer output signal responsive to the output signal of said comparator means and for storing signals representative of the digital approximations of said output signal of said spirometer means at predetermined sampling intervals to comprise said stored record.

3. The apparatus of claim 1 wherein said computer means stores data representative of which function key means is pressed prior to the acquisition of data from said spirometer means, said keyboard means further comprising print key means for actuating said computer means to compute the data called for by the function key means that had been pressed and for controlling said record generating means to generate said record.

4. The apparatus of claim 3 wherein said computer means further comprises programmed means for controlling said keyboard means during the acquisition of data from said spirometer means in response to the actuation of one of said function key means.

5. The apparatus of claim 3 wherein said computer means further comprises programmed means responsive to the actuation of separate function key means for computing forced expiratory volume data, minute ventilation data, maximal voluntary ventilation data, and functional residual capacity data for said subject responsive to the stored record of data acquired from said subject.

6. The apparatus of claim 1 wherein said printer means is a dot-matrix printer.

7. The apparatus of claim 1 wherein said transducer means further includes helium transducer means and carbon monoxide transducer means; and further comprising switching means receiving the output signals of said transducer means for coupling one of said outputs to said computer means under control of said computer means.

8. A self-contained, portable system for measuring, computing and preparing a permanent record of breathing parameters of a test subject undergoing forced, expired breathing maneuvers according to instructions, comprising: spirometer means for receiving the exhaled gases of said subject during a forced test maneuver and for generating a signal representative of the volume of gases exhaled by said subject during a predetermined breathing maneuver; programmable digital computer means receiving said signal for acquiring and storing digital signals comprising a stored record of said maneuver, said computer means being programmable for computing predetermined respiratory parameters of said subject from said stored signals; one of the test functions programmed in said computer means being a Forced Expiratory Volume test, said computer means including programmed means for converting the signal from said spirometer means into digital signal representation at a predetermined sampling rate, for determining the first measurement value of said signal from said spirometer means by comparing it to a predetermined threshold value and thereafter storing samples of the signal from said spirometer means at predetermined intervals to generate a series of stored digital samples representative of a forced expiratory volume curve; keyboard means comprising a plurality of key means communicating with said computer means and selectively actuatable by an operator and communicating with said computer means for entering data relating to said particular subject and for controlling the acquisition of said stored record of a breathing maneuver and for controlling the sequence of operation and computation of said system; and printer means for printing a permanent record under control of said computer means as selected by the operator through said keyboard means, said computer means being programmed, upon being actuated to print a message on said record instructing the operator to enter subject identification or reference data into said system by means of said keyboard means.

9. The system of claim 8 wherein said keyboard means comprises first digit key means representative of digit data and second function key means, each function key means being associated with a different respiratory parameter and, upon actuation, controlling the acquisition of data by said computer means, said computer means storing function data representative of the function key means actuated by said operator during a predetermined breathing maneuver.

10. The system of claim 9 wherein said computer means further comprises programmed means for accepting predetermined identification and reference data prior to the initiation of a test maneuver and for controlling said printer means to instruct the operator when said predetermined identification and reference data is not entered prior to the execution test.

11. The system of claim 10 wherein said computer means further comprises programmed means for printing indicia instructing the operator to select one of a predetermined number of options only after sufficient identification and reference data has been entered, said options including the acquisition of test data upon further keyboard means actuation by the operator.

12. The system of claim 9 wherein said computer means further comprises programmed means for sequentially scanning said digit key means and said function key means, and upon the recognition of the actuation of a function key, means to store information representative of the function called for, to decode the function called for, and then to proceed with acquiring data from said spirometer means for computing the function called for.

13. The system of claim 12 wherein said computer means includes push-down stack memory means for storing said samples representative of the Forced Expiratory Volume curve.

14. The system of claim 8 wherein said computer means includes programmed means for measuring maximal voluntary ventilation or minute volume, said last-mentioned programmed means sensing the actuation of a corresponding function key means and for detecting and determining successive pairs of minimum and maximum measurement values of said output signal from said spirometer means, said last-mentioned programmed means being further programmed to store a signal representative of total elapsed time for said function.

15. The system of claim 14 wherein said computer means further includes programmed means for detecting maximum values of the output signals of said spirometer means by first determining whether given samples have exceeded a previously stored minimum value by a predetermined positive slope threshold, and if so, to continue to look for true maximum values while not storing samples as maximum values if said predetermined positive slope thresholds have not been exceeded.

16. The system of claim 8 wherein said computer means includes programmed means for computing functional residual capacity, said keyboard means further including an end-of-test key means communicating with said computer means for terminating the acquisition of test data said computer means further including programmed means for detecting the actuation of said functional residual capacity function key means, to detect and store maximum and minimum values of the data acquired during the conduction of a functional residual capacity test and to compute from said stored data functional residual capacity, tidal volume, inspiratory capacity, expiratory reserve volume, and lung-diffusing capacity.

* * * * *